United States Patent
Miyasato

(10) Patent No.: US 10,342,436 B2
(45) Date of Patent: Jul. 9, 2019

(54) OBJECT INFORMATION ACQUIRING APPARATUS AND PROCESSING METHOD

(71) Applicant: CANON KABUSHIKI KAISHA, Tokyo (JP)

(72) Inventor: Takuro Miyasato, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 138 days.

(21) Appl. No.: 15/500,634

(22) PCT Filed: Aug. 21, 2015

(86) PCT No.: PCT/JP2015/004203
§ 371 (c)(1),
(2) Date: Jan. 31, 2017

(87) PCT Pub. No.: WO2016/031213
PCT Pub. Date: Mar. 3, 2016

(65) Prior Publication Data
US 2017/0215739 A1    Aug. 3, 2017

(30) Foreign Application Priority Data
Aug. 26, 2014  (JP) ................................ 2014-171679

(51) Int. Cl.
*A61B 5/00* (2006.01)
*A61B 5/145* (2006.01)
*A61B 5/107* (2006.01)

(52) U.S. Cl.
CPC ........ *A61B 5/0095* (2013.01); *A61B 5/14542* (2013.01); *A61B 5/1077* (2013.01); *A61B 5/1079* (2013.01)

(58) Field of Classification Search
CPC . A61B 5/0095; A61B 5/14542; A61B 5/1077; A61B 5/1079
See application file for complete search history.

(56) References Cited

U.S. PATENT DOCUMENTS

2010/0087733 A1*  4/2010  Nakajima ............ A61B 5/0073
                                                              600/437
2012/0271170 A1* 10/2012  Emelianov ........... A61B 5/0095
                                                              600/439
(Continued)

FOREIGN PATENT DOCUMENTS

EP       2868266 A1      5/2015
JP     2010-088627       4/2010
(Continued)

OTHER PUBLICATIONS

Office Action dated Oct. 2, 2018, in counterpart application JP 2015-165851 (6 pages).

*Primary Examiner* — Daniel Pihulic
(74) *Attorney, Agent, or Firm* — Venable LLP

(57) ABSTRACT

An object information acquiring apparatus, comprises an irradiating unit configured to irradiates an object with pulsed light; an acoustic wave detection unit configured to detect an acoustic wave generated from the object irradiated with the pulsed light and convert the acoustic wave into an electric signal; a storage unit configured to store a normalized light fluence distribution, which is a light fluence distribution normalized for a region of a predetermined size; and a processing unit configured to acquire characteristic information on the object using the stored normalized light fluence distribution and the electric signal.

21 Claims, 13 Drawing Sheets

(56) References Cited

U.S. PATENT DOCUMENTS

| | | | |
|---|---|---|---|
| 2013/0006088 A1 | 1/2013 | Miyasato | |
| 2013/0035570 A1 | 2/2013 | Miyasato | |
| 2013/0338498 A1* | 12/2013 | Emelianov | A61B 8/12 |
| | | | 600/431 |
| 2014/0036636 A1 | 2/2014 | Miyasato | 367/178 |
| 2014/0046165 A1* | 2/2014 | Fukutani | A61B 5/0095 |
| | | | 600/407 |
| 2014/0296690 A1 | 10/2014 | Miyasato et al. | 600/407 |
| 2015/0238090 A1 | 8/2015 | Suita et al. | A61B 5/0095 |
| 2016/0174849 A1 | 6/2016 | Nanaumi et al. | A61B 5/0095 |
| 2016/0305914 A1* | 10/2016 | Wang | G02B 21/0004 |
| 2017/0215739 A1* | 8/2017 | Miyasato | A61B 5/0095 |
| 2018/0011061 A1* | 1/2018 | Furukawa | A61B 5/0091 |

FOREIGN PATENT DOCUMENTS

| | | | |
|---|---|---|---|
| JP | 2011-206192 A | 10/2011 | |
| JP | 2012-125447 | 7/2012 | |
| JP | 2013-52227 A | 3/2013 | |
| JP | 2013-103021 A | 5/2013 | |
| JP | 2016047237 A * | 4/2016 | A61B 5/0095 |
| WO | 2010/024290 A1 | 3/2010 | |
| WO | WO-2016031213 A1 * | 3/2016 | A61B 5/0095 |

\* cited by examiner

[Fig. 2]
FIG. 2A STATE 1
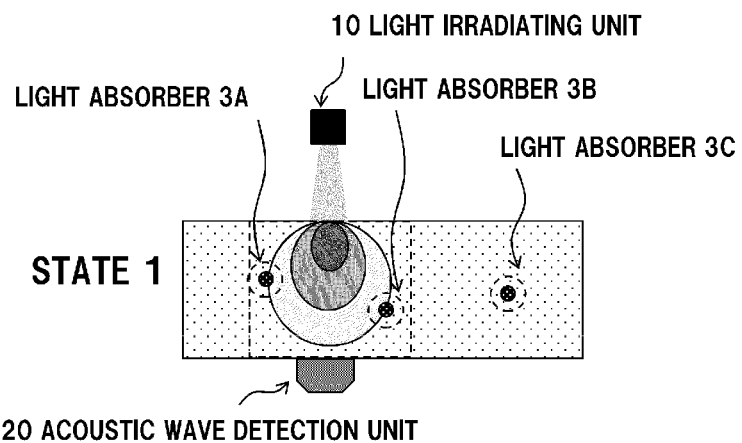
FIG. 2B STATE 2
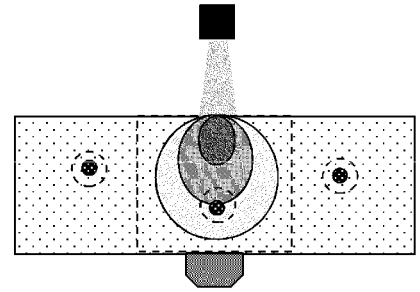
FIG. 2C STATE 3
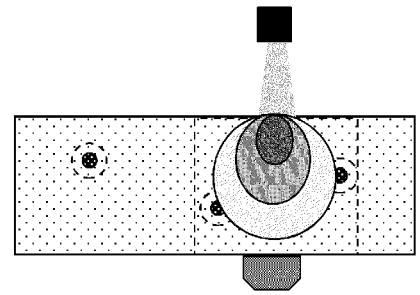

[Fig. 7]
FIG. 7A  STATE 1
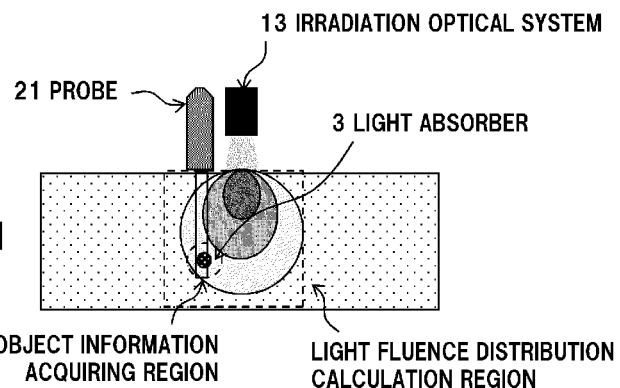
FIG. 7B  STATE 2
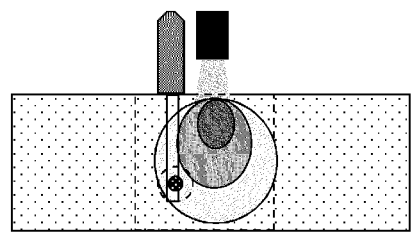
FIG. 7C  STATE 3
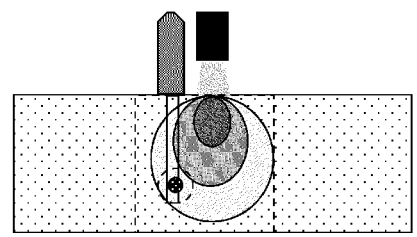

[Fig. 9]
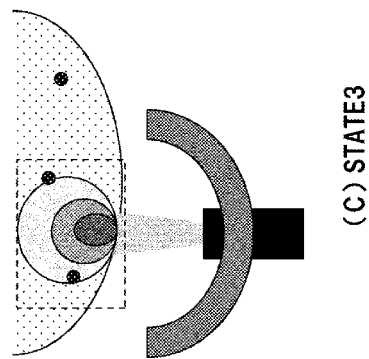
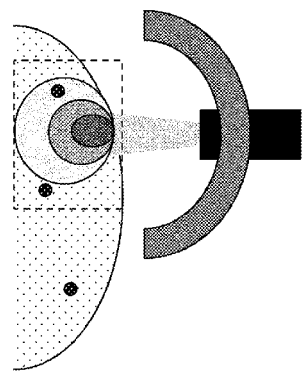
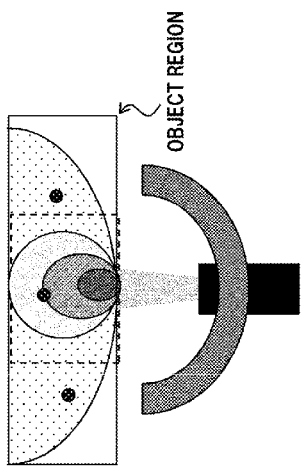
FIG. 9A (A) STATE1
FIG. 9B (B) STATE2
FIG. 9C (C) STATE3

[Fig. 10]

[Fig. 13]
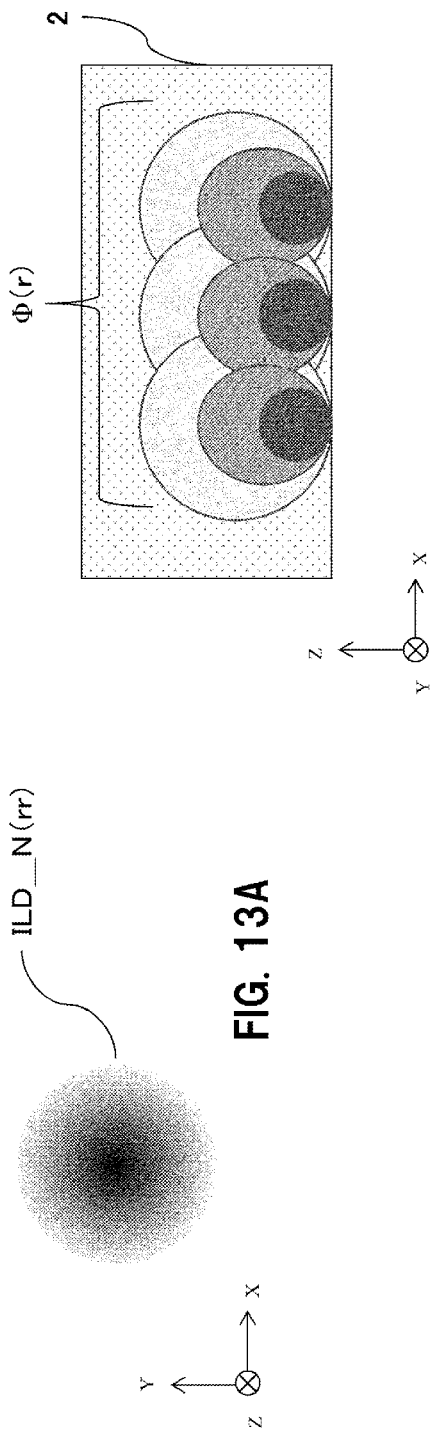
FIG. 13A
FIG. 13B
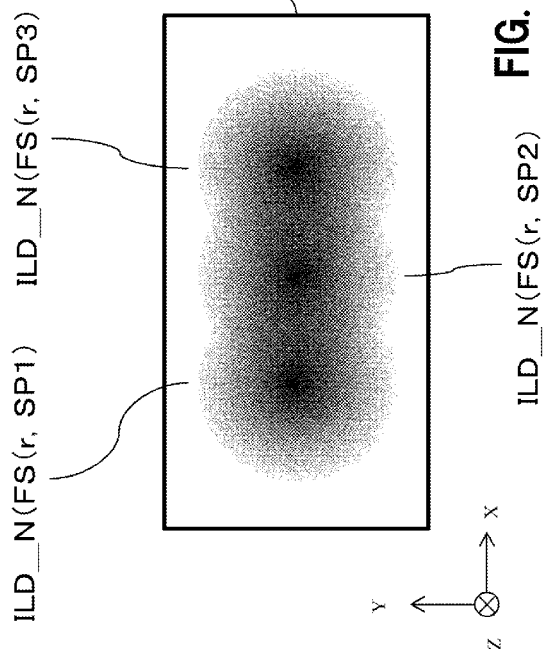
FIG. 13C

OBJECT INFORMATION ACQUIRING APPARATUS AND PROCESSING METHOD

TECHNICAL FIELD

The present invention relates to an object information acquiring apparatus configured to acquire information on the interior of an object.

BACKGROUND ART

As an optical imaging technique, photoacoustic tomography (PAT) has been proposed lately.

If a living body (object) is irradiated with light, such as pulsed laser light, an acoustic wave is generated when the light is absorbed by biological tissue inside the object. This phenomena is called a "photoacoustic effect", and an acoustic wave generated by the photoacoustic effect is called a "photoacoustic wave". The tissues that constitute an object have different light energy absorption rates respectively, hence the sound pressure of the photoacoustic wave to be generated from each tissue is also different. In PAT, the generated photoacoustic wave is detected by a probe, and the detected signal is mathematically analyzed, whereby an optical characteristic inside the object, particularly the distribution of the light energy absorption density, can be imaged.

A major technique to calculate the initial sound pressure of the acoustic wave generated inside the object is the back projection method. The initial sound pressure $P_0$ of the acoustic wave generated from a light absorber inside the object is given by Expression (1).

$$P_0 = \Gamma \cdot \mu_a \cdot \Phi \qquad \text{Expression(1)}$$

Here $\Gamma$ is a Gruneisen coefficient, and is determined by dividing the product of the volume expansion coefficient $\beta$ and the square of the sound velocity c by a specific heat at constant pressure $C_p$. It is known that $\Gamma$ is approximately constant once the object is determined. $\mu_a$ is a light absorption coefficient of an absorber, and $\Phi$ is a light fluence [J/m² or J/m³] in a local region of the object.

Patent Literature 1 discloses a technique to measure by an acoustic wave detector the temporal change of the sound pressure P of an acoustic wave propagated through an object, and calculate the initial sound pressure distribution based on the measurement result. By dividing the calculated initial sound pressure distribution by the Gruneisen coefficient $\Gamma$, the product of $\mu_a$ and $\Phi$, that is, the absorption density of the light energy, can be acquired.

The Gruneisen coefficient is approximately constant for each object, hence the light fluence distribution inside the object must be determined in order to acquire the distribution of the light absorption coefficient $\mu_a$ from the distribution of the initial sound pressure $P_0$.

CITATION LIST

Patent Literature

[Patent Literature 1] Japanese Patent Application Laid-Open No. 2010-88627

SUMMARY OF INVENTION

Technical Problem

As mentioned above, the light fluence distribution inside the object must be accurately determined to determine the light absorption coefficient distribution inside the object with accuracy. For this, the light fluence distribution must be determined each time the pulsed light is radiated, which increases calculation cost.

With the foregoing in view, it is an object of the present invention to suppress the calculation cost in the object information acquiring apparatus utilizing the photoacoustic effect.

Solution to Problem

The present invention in its one aspect provides an object information acquiring apparatus, comprises an irradiating unit configured to irradiates an object with pulsed light; an acoustic wave detection unit configured to detect an acoustic wave generated from the object irradiated with the pulsed light and convert the acoustic wave into an electric signal; a storage unit configured to store a normalized light fluence distribution, which is a light fluence distribution normalized for a region of a predetermined size; and a processing unit configured to acquire characteristic information on the object using the stored normalized light fluence distribution and the electric signal.

The present invention in its another aspect provides a processing method to acquire characteristic information on an object irradiated with pulsed light based on an electric signal outputted by detecting an acoustic wave generated from the object, the method comprises a step of reading a normalized light fluence distribution, which is a light fluence distribution normalized for a region of a predetermined size, and is stored in a storage unit; and a step of acquiring the characteristic information on the object using the normalized light fluence distribution and the electric signal.

Advantageous Effects of Invention

According to the present invention, the calculation cost can be suppressed in the object information acquiring apparatus utilizing the photoacoustic effect.

Further features of the present invention will become apparent from the following description of exemplary embodiments with reference to the attached drawings.

BRIEF DESCRIPTION OF DRAWINGS

FIG. 2A to FIG. 2C are diagrams depicting the positional relationship of the light irradiating unit and the acoustic wave detection unit with respect to the object.

FIG. 7A to FIG. 7C are diagrams depicting the positional relationship of the light irradiating unit and the acoustic wave detection unit with respect to the object.

FIG. 9A to FIG. 9C are diagrams depicting the positional relationship of the light irradiating unit and the acoustic wave detection unit with respect to the object.

FIG. 13A to FIG. 13C are diagrams depicting the light fluence distribution calculation using the average of sum of irradiating light fluence distribution.

DESCRIPTION OF EMBODIMENTS

Figure 1:
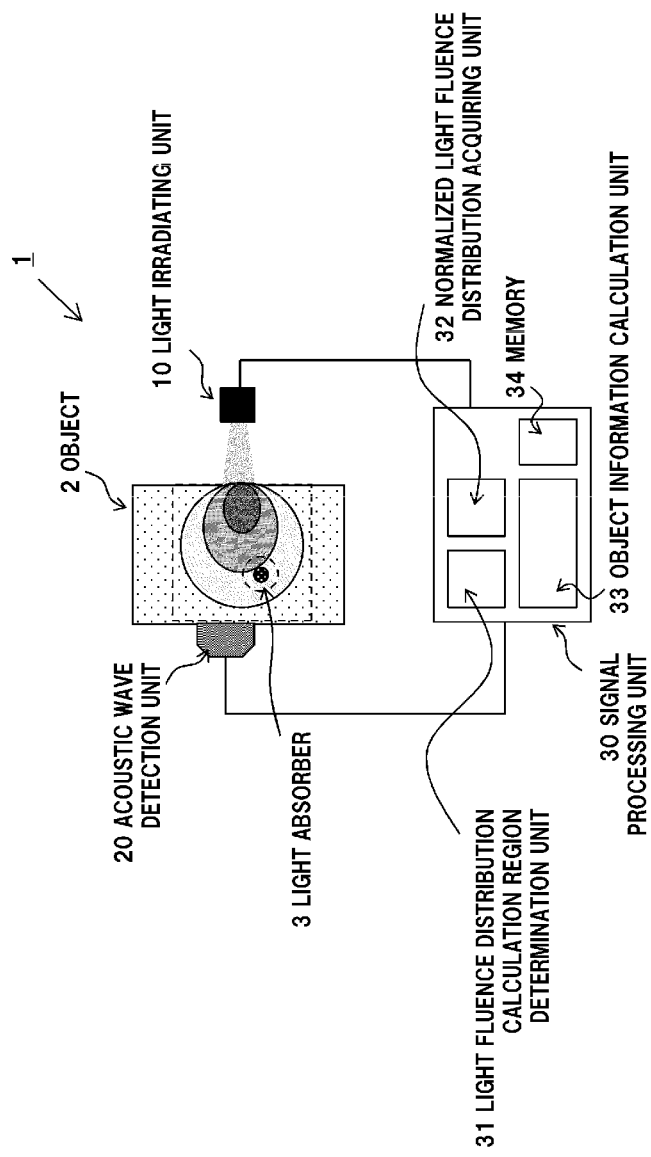
FIG. 1 is a system block diagram of a photoacoustic measuring apparatus according to Embodiment 1.

Embodiments of the present invention will now be described with reference to the drawings. As a rule, a same composing element is denoted with a same reference numeral, and explanation thereof is omitted. Numeric values, materials, shapes, positions or the like used in the description of the embodiments should be appropriately changed in accordance with the configuration of an apparatus and various conditions to which the invention is applied, and are not intended to limit the scope of the invention.

In Embodiment 1, a minimal configuration to carry out the invention will be described first, then concrete variations of the apparatus will be described in Embodiments 2 to 4.

Embodiment 1

An object information acquiring apparatus according to Embodiment 1 is an apparatus that irradiates an object with pulsed light, and visualizes (images) the characteristic information inside the object by detecting and analyzing a photoacoustic wave generated inside the object due to the pulsed light. The characteristic information in this description refers to information related to a light absorption coefficient inside the object, such as light absorption coefficient distribution, light absorption energy density distribution and spectral information (e.g. oxygen saturation degree) based on the light absorption coefficient acquired at a plurality of wavelengths.

The object information acquiring apparatus according to this embodiment is called a "photoacoustic measuring apparatus".
<System Configuration>
A configuration of the photoacoustic measuring apparatus 1 according to this embodiment will be described with reference to FIG. 1. The photoacoustic measuring apparatus 1 according to this embodiment has a light irradiating unit 10, an acoustic wave detection unit 20, and a signal processing unit 30. The signal processing unit 30 includes: a light fluence distribution calculation region determination unit 31; a normalized light fluence distribution acquiring unit 32; and an object information calculation unit 33. The reference numeral 2 indicates a part of a living body (object), and the reference numeral 3 indicates a light absorber inside the object.

Now each unit constituting the photoacoustic measuring apparatus according to this embodiment will be described, whereby an overview of the measurement method is presented.
<<Light Irradiating Unit 10>>
The light irradiating unit 10 is a unit to generate pulsed light and irradiate an object with the pulsed light, and is constituted by a light source and an irradiation optical system (neither are illustrated).

The light source is preferably a laser light source because of high output, but a light emitting diode, a flash lamp or the like may be used instead of laser. In the case of using a laser for the light source, various types can be used, such as a solid-state laser, gas laser, dye laser and semiconductor laser.

Ideally an Nd:YAG-excited Ti-sa laser or alexandrite laser is used because the output is high and wavelength can be continuously changed. A plurality of single wavelength lasers having different wavelengths may be used.

Radiation timing, waveform, intensity or the like is controlled by a light source control unit (not illustrated). This light source control unit may be integrated with the light source.

The wavelength of the pulsed light is a specific wavelength that is absorbed by a specific component out of the components constituting the object, and is preferably a wavelength at which the light can propagate inside of the object. In concrete terms, 700 nm or more to 1100 nm or less is preferable if the object is a living body.

To effectively generate the photoacoustic wave, light must be radiated in a sufficiently short time in accordance with the thermal characteristic of the object. If the object is a living body, the pulse width of the pulsed light generated from the light source is preferably about 10 nanoseconds to 50 nanoseconds. The pulsed light generated from the light source is hereafter called an "irradiating light".

The irradiation optical system is a unit that radiates the pulsed light, emitted from the light source, into the object. The irradiation optical system normally guides the irradiating light to the object while processing the light into a desired irradiating light distribution shape, using such optical members as a mirror to reflect the light, a lens to magnify the light, and a diffusion plate to diffuse the light, but may propagate the light using a waveguide, such as an optical fiber. For these optical components, any component may be used as long as the irradiating light emitted from the light source can irradiate the object 2 in a desired shape. It is preferable that the light is expanded to a certain area instead of being collected by a lens, in terms of safety of the object and widening of the diagnostic region. To change the position irradiated with the irradiating light, a scanning mechanism may be disposed in the irradiation optical system.
<<Acoustic Wave Detection Unit 20>>
The acoustic wave detection unit 20 is a unit to detect an acoustic wave generated inside the object and convert it into an electric signal (photoacoustic wave signal). The acoustic wave detection unit is also called a "probe", an "acoustic wave detector" or a "transducer". The acoustic wave in the present invention is typically an ultrasonic wave, and includes an elastic wave called a "sound wave", an "ultrasonic wave", a "photoacoustic wave" and a "light induced ultrasonic wave".

The acoustic wave generated from a living body is an ultrasonic wave in a 100 KHz to 100 MHz range, hence an ultrasonic detector that can detect this frequency band is used for the acoustic wave detection unit 20. In concrete terms, a transducer based on a piezoelectric phenomenon, a transducer based on the resonance of light, a transducer based on capacitance change or the like can be used. It is preferable that the acoustic wave detection unit 20 has high sensitivity and a wide frequency band.

The acoustic wave detection unit 20 may be a unit in which a plurality of detection elements are one-dimensionally or two-dimensionally disposed, and which can be moved by a scanning mechanism. If multi-dimensionally arrayed elements are used, an acoustic wave can be detected simultaneously at a plurality of locations, which can shorten the measuring time and reduce the influence of vibration of the object. A single element focused by an acoustic lens may be used.

The acoustic wave detection unit 20 also includes a unit to amplify the acquired electric signal and convert the amplified electric signal into a digital signal. In concrete terms, the acoustic wave detection unit 20 includes an amplifier, an A/D converter, an FPGA chip or the like.

If a plurality of detection signals is acquired, it is preferable to process the plurality of signals simultaneously. Then time until generating the image can be shortened.

Acoustic wave signals detected at a same position with respect to the object may be integrated into one signal. The integration method may be adding the signals or determining an average thereof. The signals may be added with weighting respectively.

The "detection signal" in this description is a concept that includes both an analog signal outputted from the acoustic wave detection unit, and a digital signal generated by A/D conversion thereafter.

<<Signal Processing Unit 30>>

The signal processing unit 30 is a unit to process the converted digital signal and reconstruct an image representing the optical characteristic inside the object. For the reconstruction, any available method can be used, such as a Fourier transform method, a universal back projection method (UBP method), and a filtered back projection method. The generated image is presented to the user by a display device (not illustrated).

The signal processing unit 30 includes: a light fluence distribution calculation region determination unit 31; a normalized light fluence distribution acquiring unit 32; and an object information calculation unit 33. Concrete operation of each unit will be described later.

The signal processing unit 30 may be an independent computer that includes a CPU, a main storage and auxiliary storage, or may be designed as dedicated hardware.

For the signal processing unit 30, a workstation is normally used, where the above mentioned processing is executed by software. For example, the above mentioned light fluence distribution calculation region determination unit 31, normalized light fluence distribution acquiring unit 32, and object information calculation unit 33 may be executed by corresponding software respectively. Each unit may be independent hardware. In this case, each hardware is collectively called a "signal processing unit 30".

<Object Measuring Method>

Now a method for measuring a living body (object) by the photoacoustic measuring apparatus according to this embodiment will be described.

First, the object is irradiated with the irradiating light emitted from the light irradiating unit 10. The irradiating light that entered into the object decays while repeating diffusion/absorption inside the object (inside the biological tissue if the object is a living body), and forms a light fluence distribution in accordance with the distance from the irradiation position or the like.

If a part of the energy of the light that propagated through the living body is absorbed by a light absorber, such as blood, an acoustic wave is generated from this light absorber by thermal expansion. For example, if a cancer exists in the living body, light is specifically absorbed by the new blood vessels of the cancer, just like the blood vessels of normal regions, and an acoustic wave is generated.

The generated acoustic wave propagates through the object, is detected by the acoustic wave detection unit 20, and is converted into an analog electric signal. The acoustic wave detection unit 20 in this embodiment has an acoustic wave detection element (not illustrated) that includes a focus type acoustic lens, so that the position where the acoustic wave was generated can be specified.

The acoustic wave detection unit 20 amplifies the electric signal, converts the amplified electric signal into a digital signal, and stores this detection signal in the memory 34 (storage unit) inside the signal processing unit 30.

Now an overview of the processing to acquire the optical characteristic inside the object from the detection signal stored in the signal processing unit 30 will be described.

As mentioned above, the initial sound pressure inside the object is in proportion to the light absorption coefficient of the light absorber and the light fluence of the irradiating light that reached the light absorber. In other words, the light fluence distribution of the irradiating light in the object must be acquired to determine the distribution of the light absorption coefficient inside the object.

First the light fluence distribution calculation region determination unit 31 determines a region, for which the distribution of the irradiating light with which the object is irradiated (hereafter called a "light fluence distribution calculation region"). The light fluence distribution calculation region is determined using the profile of the irradiating light (the light fluence distribution of the irradiating light), an average optical coefficient of the object, a shape of the object, and an estimated absorption coefficient of the light absorber.

Then the normalized light fluence distribution acquiring unit 32 acquires the light fluence distribution inside the object when the light fluence of the irradiating light is normalized using the profile of the irradiating light and the average optical coefficient of the object (hereafter called a "normalized light fluence distribution").

Finally the object information calculation unit 33 acquires the optical characteristic distribution inside the object using the light intensity [J] of the irradiating light with which the object is actually irradiated, the normalized light fluence distribution, and the detection signal. The acquired optical characteristic distribution is converted into image data, and is outputted to the display device (not illustrated).

Concrete processing executed by the light fluence distribution calculation region determination unit 31, the normalized light fluence distribution acquiring unit 32 and the object information calculation unit 33, and the effects thereof will be described later.

<Optical Characteristic Distribution Acquiring Method>

A conventional method to acquire the optical characteristic distribution inside the object, when the object is irradiated with the irradiating light for a plurality of times, will be described next.

In this example, as illustrated in FIG. 2A to FIG. 2C, it is assumed that the light irradiating unit 10 and the acoustic wave detection unit 20 respectively are scanned relative to the object, and radiation of the irradiating light and acquisition of the acoustic wave are implemented at a plurality of locations. Here the relative positional relationship of the object 2, the light absorbers 3A to 3C, the light irradiating unit 10, and the acoustic wave detection unit 20 is called a "state". In concrete terms, the positional relationships illustrated in FIG. 2A, FIG. 2B and FIG. 2C are called "state 1", "state 2" and "state 3" respectively. In the following description, the state number is used to distinguish each state.

Here it is assumed that the positions of the light absorbers 3A, 3B and 3C are rA, rB and rC, and the absorption coefficients thereof are μt(rA), μt(rB) and μt(rC) respectively.

Further, it is assumed that the actual light fluence distributions in state 1, state 2 and state 3 are Φ1t(r), Φ2t(r) and Φ3t(r) respectively.

Further, it is assumed that the actual initial sound pressure distributions in state 1, state 2 and state 3 are P1t(r), P2t(r) and P3t(r) respectively. r is a positional coordinate inside the object.

Further, it is assumed that the detection signals in state 1, state 2 and state 3 are S1(r), S2(r) and S3(r) respectively. If the acoustic detection unit has a plurality of probe elements, a detection signal group, constituted by a plurality of detection signals, is acquired, but in this case, S1(r), S2(r) and S3(r) denote detection signal groups in state 1 to state 3 respectively.

Further, it is assumed that the initial sound pressure distributions acquired by reconstructing the detection signals using the UBP method or the like respectively are Pi1(r), Pi2(r) and Pi3(r), and the initial sound pressure distribution reconstructed using all the detected signals is Pi(r).

If the above mentioned Expression (1) is used, the initial sound pressure in each light absorber is given by the following Expression (2) to Expression (4). To simplify description, it is assumed that the Gruneisen coefficient Γ is 1, and the initial sound pressure acquired from the detection signal is R(S(r)). In other words, Pi(r)=R(S(r)).

$$Pi(rA) = \frac{\{P1i(rA) + P2i(rA) + P3i(rA)\}}{3}$$
$$= \frac{\{R(S1(rA)) + R(S2(rA)) + R(S3(rA))\}}{3}$$
$$= R(S1(rA), S2(rA), S3(rA)) \quad \text{Expression (2)}$$

$$Pi(rB) = \frac{\{P1i(rB) + P2i(rB) + P3i(rB)\}}{3}$$
$$= \frac{\{R(S1(rB)) + R(S2(rB)) + R(S3(rB))\}}{3}$$
$$= R(S1(rB), S2(rB), S3(rb)) \quad \text{Expression (3)}$$

$$Pi(rC) = \frac{\{P1i(rC) + P2i(rC) + P3i(rC)\}}{3}$$
$$= \frac{\{R(S1(rC)) + R(S2(rC)) + R(S3(rC))\}}{3}$$
$$= R(S1(rC), S2(rC), S3(rC)) \quad \text{Expression (4)}$$

The absorption coefficient μi(rA) of the light absorber A is calculated by Expression (5), using Expression (1) and Expression (2) when the light fluence distribution calculated in each state is Φ1i(r), Φ2i(r) and Φ3i(r).

$$\mu i(rA)=R(S1(rA),S2(rA),S3(rA))/\{(\Phi 1i(rA)+\Phi 2i(rA)+\Phi 3i(rA))/3\} \quad \text{Expression (5)}$$

The absorption coefficient μi(rB) of the light absorber B is calculated by Expression (6) using Expression (1) and Expression (3).

$$\mu i(rB)=P(rB)/\{(\Phi 1(rB)+\Phi 2(rB)+\Phi 3(rB))/3\}=R(S1(rB),S2(rB),S3(rB))/\{(\Phi 1i(rB)+\Phi 2i(rB)+\Phi 3i(rB))/3\} \quad \text{Expression (6)}$$

The absorption coefficient μi(rC) of the light absorber C is calculated by Expression (7) using Expression (1) and Expression (4).

$$\mu i(rC)=3\cdot P(rC)/\{\Phi 1(rC)+\Phi 2(rC)+\Phi 3(rC)\}=3\cdot R(S1(rC),S2(rC),S3(rC))/\{(\Phi 1i(rC)+\Phi 2i(rC)+\Phi 3i(rC))/3\} \quad \text{Expression (7)}$$

In this example, as a method for calculating the initial sound pressure when irradiation is performed for a plurality of times, a method of adding and averaging the initial sound pressure calculated in each irradiation is used, as shown in Expressions (2), (3) and (4). Therefore the denominator (light fluence) in Expressions (5), (6) and (7), to calculate the absorption coefficient, is divided by the number of times of irradiation. However, the following expression may be used as a method for calculating the initial sound pressure when irradiation is performed a plurality of times.

$$P'i(rA) = \{P1i(rA) + P2i(rA) + P3i(rA)\}$$
$$= \{R(S1(rA)) + R(S2(rA)) + R(S3(rA))\}$$
$$= R'(S1(rA), S2(rA), S3(rA))$$

In this case, the absorption coefficient can be calculated using the following expression.

$$\mu i(rA)=R'(S1(rA),S2(rA),S3(rA))/\{(\Phi 1i(rA)+\Phi 2i(rA)+\Phi 3i(rA))\}$$

Both methods can be used for all embodiments disclosed in this description, but here the integration average method is used for simplification.

The light fluence distribution Φi(r) can be determined by measuring beforehand the irradiating light fluence distribution O on the surface of object 2, and calculating the diffusion equation or the transfer equation, based on the irradiating light fluence distribution O(r) as a source and using the finite element method, the finite volume method, the difference method or the like.

The light fluence distribution Φi(r) can also be determined by obtaining an analytical solution of the diffused light propagation or light propagation using the Monte Carlo method. Any method may be used if the light fluence can be calculated. It is preferable that the light irradiating unit 10 radiates pulsed light so that the irradiating light fluence distribution O(r) is the same on the surface positions of the object 2, in a range that does not exceed allowable errors of the object information that is finally calculated.

Now the actual light fluence distribution and the initial sound pressure distribution will be described using actual values. Here it is assumed that the object is a rectangular parallelepiped of which height is 50 mm, width is 120 mm and depth is 120 mm. It is also assumed that the average absorption coefficient μaM of the object is 0.005/mm, and the average equivalent scattering coefficient μs'M is 0.85/mm. The average absorption coefficient is an absorption coefficient generated by equalizing the absorption coefficients of the entire region of object 2, and the average equivalent scattering coefficient is an equivalent scattering coefficient generated by equalizing the scattering coefficients of the entire region of object 2.

It is assumed that the surface of the object 2 is evenly irradiated with the irradiating light in a 30 mm diameter circular shape, and the light intensity thereof is 100 mJ in state 1, 125 mJ in state 2, and 80 mJ in state 3. It is also assumed that the absorber A, the absorber B and the absorber C are blood vessels, and the absorption coefficient μ is 150/m.

When the above values are used, the actual light fluence at each absorber position becomes as follows respectively.

$\Phi 1t(rA)=50$ J/m², $\Phi 1t(rB)=3$ J/m², $\Phi 1t(rC)=0.003$ J/m²

$\Phi 2t(rA)=0.02$ J/m², $\Phi 2t(rB)=500$ J/m², $\Phi 2t(rC)=0.03$ J/m²

$\Phi 3t(rA)=0.0007$ J/m², $\Phi 3t(rB)=4$ J/m², $\Phi 3t(rC)=20$ J/m²

The actual initial sound pressure at each absorber position becomes as follows respectively.

$P1t(rA)=7500$ Pa, $P1t(rB)=450$ Pa, $P1t(rC)=0.45$ Pa $P2t(rA)=3$ Pa, $P2t(rB)=75000$ Pa, $P2t(rC)=4.5$ Pa $P3t(rA)=0.105$ Pa, $P3t(rB)=600$ Pa, $P3t(rC)=3000$ Pa

An example when the actual light fluence distribution and the initial sound pressure distribution described above are determined by calculation will now be described. The light fluence distribution can be acquired by calculating the propagation of light based on the average absorption coefficient of the object, the average scattering coefficient, the irradiating light fluence distribution O on the surface of the object, and the shape of the object. The initial sound pressure distribution can be acquired by reconstructing the detection signal.

Here it is assumed that the light fluence distribution and the initial sound pressure distribution can be accurately calculated as follows respectively.

$\Phi 1i(rA)=50$ J/m², $\Phi 1i(rB)=1.5$ J/m², $\Phi 1i(rC)=0.003$ J/m²

$\Phi 2i(rA)=0.02$ J/m², $\Phi 2i(rB)=500$ J/m², $\Phi 2i(rC)=0.03$ J/m²

$\Phi 3i(rA)=0.0007$ J/m², $\Phi 3i(rB)=2$ J/m², $\Phi 3i(rC)=20$ J/m²

$P1i(rA)=7500$ Pa, $P1i(rB)=225$ Pa, $P1i(rC)=0.45$ Pa $P2i(rA)=3$ Pa, $P2i(rB)=75000$ Pa, $P_2i(rC)=3$ Pa $P3i(rA)=0.105$ Pa, $P3i(rB)=300$ Pa, $P3i(rC)=3000$ Pa

Then the absorption coefficient of each light absorber is calculated. If the above mentioned values are applied to Expression (5), Expression (6) and Expression (7), each absorption coefficient is calculated as follows.

$\mu(rA)=\{(7500+3+0.105)/3\}/\{(50+0.02+0.007)/3\}=150$/m $\mu(rB)=\{(225+75000+300)/3\}/\{(1.5+500+2)/3\}=150$/m $\mu(rC)=\{(0.45+4.5+3000)/3\}/\{(0.003+0.03+20)/3\}=150$/m

The absorption coefficient (true value: 150/m) in the object can be calculated by the method described above.

However, in the case of the above mentioned method, the light fluence distribution on the entire region (120 mm×120 mm×50 mm) must be calculated even if only a part of the object 2 is irradiated with the irradiating light. For example, if resolution is a 1 mm×1 mm×1 mm voxel, the operation must be performed for 120×120×50=720,000 voxels, which makes the calculation cost extremely high. In other words, a first problem is that operation is performed for an unnecessary region.

Moreover, as mentioned above, the light fluence distribution must be determined by a diffusion equation, a transfer equation or the like, which makes the calculation cost enormous. Further, as the number of times of irradiation of the pulsed light increases, the operation amount increases proportionally. In other words, a second problem is that an operation amount to determine the light fluence distribution is large from the outset.

Therefore these two problems are solved in this embodiment by using the configurations described in the following sections (1) and (2).

(1) Reduction of Operation Amount by Limiting Light Fluence Distribution Calculation Region In this embodiment, a region excluding a region where the irradiating light reaching this region is very weak and which does not exert much influence on the calculation of the absorption coefficient, in other words, a region that has major influence on the calculation of the absorption coefficient (light fluence distribution calculation region), is set, and the light fluence distribution thereof is calculated. The light fluence calculation region is determined by the light fluence distribution calculation region determination unit 31.

The light fluence distribution calculation region can be determined based on the light fluence distribution on the surface of the object when the irradiating light enters, the shape of the object, and the fluence distribution estimated from the average absorption coefficient and the average scattering coefficient, for example. The light fluence distribution calculation region may be determined based on the spatial sensitivity distribution using directivity, sensitivity or the like of the probe, or the spatial sensitivity distribution that is measured in advance. The light fluence distribution calculation region may be determined based on the absorption coefficient of the observation target light absorber, and the shape thereof.

For example, it is assumed that the observation target light absorber is a blood vessel of which diameter is 500 μm, and the absorption coefficient $\mu_{target}$ at a 797 nm wavelength is about 0.2/mm. It is also assumed that the light fluence $\Phi 0$ of the irradiating light is 200 J/m2. It is also assumed that the NEP (Noise Equivalent Pressure) of one element of the acoustic wave detection unit, when an acoustic wave having a central frequency of 3 MHz is generated, is 1 Pa. If a voxel H, of which the distance rov from the acoustic wave detection unit is 35 mm, and whose distance rvd from the surface when the irradiating light enters is 30 mm, is considered here, $\Phi$ (rov)=0.6 J/m2 is established based on Expression (8):

$$\Phi(rov)=\Phi 0\exp(-u_{e\!f\!f}\cdot rov)/rov \qquad \text{Expression (8)}$$

$\Phi$ (rov) is the light fluence at the distance rov from the incident position of the irradiating light to the target voxel, $\Phi 0$ is the light fluence on the incident surface (skin) of the irradiating light, and $u_{e\!f\!f}$ is the light decay coefficient. If the object is a human breast, $u_{e\!f\!f}$ is about 0.08/mm. The initial sound pressure of the acoustic wave, which is generated when 0.6 J/m² of light fluence reaches a light absorber of which absorption coefficient is 0.2/mm, is 120 Pa. The distance from this voxel to the acoustic wave detection unit is rvd=35 mm. On the other hand, the sound pressure of the acoustic wave that reaches the acoustic wave detection unit is 20.28 Pa, since the acoustic wave decays at a $1/\sqrt{rvd}$ decay rate.

Here it is assumed that the target voxel is at a 30° position from the front direction of the acoustic wave detection unit, and the acoustic wave that reached from the voxel H enters the front face of the probe in a 30° inclined state. The sensitivity of the acoustic wave detection unit at frequency 3 MHz at a 30° directional angle is 1/20 of the front face, therefore the acoustic wave having a 20.28 Pa of sound pressure is detected as an approximate 1 Pa signal. NEP, on the other hand, is 1 Pa, which means that the SNR (signal to noise ratio) is 1. If the probe has ten elements and noise is white noise, then the SNR becomes $1/(1\sqrt{10})=3.16$.

In this way, the SNR at a voxel is easily determined using Expression (9).

$$SNR=(\mu_{target}\cdot\Phi 0\cdot\exp(-u_{eff}\cdot rov)/rov)/\sqrt{rvd\cdot AS(\theta)/(NEP(f)/\sqrt{N})} \quad \text{Expression (9)}$$

Here $AS(\theta)$ is the detection sensitivity of the front face of the acoustic wave detection unit when the acoustic wave entered at angle $\theta$ from the front direction of the acoustic wave detection unit. N is a number of probes or a number of times of measurement. NEP(f) is NEP at the central frequency f.

It is assumed that the observation target light absorber is a blood vessel of which diameter is 500 μm, the absorption coefficient is 0.2/mm, and the SNR=3 must be acquired using a probe of which NEP at 3 MHz is 1 Pa and directional sensitivity is cos θ. In this case, the light fluence distribution calculation area is set to about 50 mm×50 mm×50 mm according to Expression (9).

For a region other than the light fluence distribution calculation region, the light fluence of the pulsed light that reaches the region is assumed to be 0.

The dotted lines in FIG. 2A to FIG. 2C indicate the light fluence distribution calculation region determined by the light fluence distribution calculation region determination unit 31. Now an error of the operation result, when the light fluence distribution calculation region is set like this, will be described. The light fluence calculated for the light absorbers A to C in FIG. 2A to FIG. 2C become as follows respectively. The initial sound pressure is assumed to be the same.

$$\Phi 1i(rA)=50 \text{ J/m}^2, \Phi 1i(rB)=3 \text{ J/m}^2, \Phi 1i(rC)=0 \text{ J/m}^2$$

$$\Phi 2i(rA)=0 \text{ J/m}^2, \Phi 2i(rB)=500 \text{ J/m}^2, \Phi 2i(rC)=0 \text{ J/m}^2$$

$$\Phi 3i(rA)=0 \text{ J/m}^2, \Phi 3i(rB)=4 \text{ J/m}^2, \Phi 3i(rC)=20 \text{ J/m}^2$$

Then the absorption coefficient of each light absorber is calculated. If the above mentioned values are applied to Expression (5), Expression (6) and Expression (7), the absorption coefficients become as follows.

$$\mu i(rA)=\{(7500+3+0.105)/3\}/\{(50+0+0)/3\}=150.0621/m$$

$$\mu i(rB)=\{(225+75000+300)/3\}/\{(0+500+0)/3\}=151.05/m$$

$$\mu i(rC)=\{(0.45+4.5+3000)/3\}/\{(0+0+20)/3\}=150.02/m$$

In other words, the absorption coefficient can be calculated at a 1% or less error from the true value 150/m.

Further, when the method of calculating the initial sound pressure distribution is improved and the absorption coefficient of each light absorber is calculated assuming that the initial sound pressure in a region other than the light fluence distribution calculation region is 0, then the result will be as follows.

$$\mu i(rA)=\{(7500+0+0)/3\}/\{(50+0+0)/3\}=150/m$$

$$\mu i(rB)=\{(0+75000+0)/3\}/\{(0+500+0)/3\}=150/m$$

$$\mu i(rC)=\{(0+0+3000)/3\}/\{(0+0+20)/3\}=150/m$$

As described above, the light fluence distribution calculation region is set in this embodiment, whereby the operation target voxels (720,000 voxels) can be reduced to 50×50×50=125,000 voxels. In other words, the calculation speed can be faster by $(720,000/125,000)^2 \approx 33$ times.

The absorption coefficient and shape of the observation target light absorber and the NEP and directivity of the probe may be inputted by the operator of the apparatus via the input unit, or may be stored in the apparatus in advance. In this example, the light fluence distribution calculation region is determined based on the light fluence distribution inside the object and the sensitivity of the probe, but only the light fluence distribution may be used, or only the sensitivity of the probe may be used.

(2) Reduction of Operation Amount by Using Normalized Light Fluence Distribution As mentioned above, the light fluence distribution must be determined by a diffusion equation or a transfer equation, which is very costly. Moreover, as the number of times of irradiation of the pulsed light increases, the operation amount increases proportionally. Therefore in this embodiment, the normalized light fluence distribution is provided in advance, and the light fluence distribution at each irradiation is determined by multiplying the normalized light fluence distribution by the output of the pulsed light.

In concrete terms, an irradiating light fluence distribution O' where the total light intensity of an irradiating light fluence distribution O is normalized to 1 mJ (hereafter called "normalized irradiating light fluence distribution") is calculated based on the profile of the irradiating light. Then based on the normalized irradiating light fluence distribution and the optical coefficient of the object (e.g. average absorption coefficient or average scattering coefficient), the distribution of normalized light fluence (normalized light fluence distribution) $\Phi N(rr)$ in the light fluence distribution region is calculated. Here rr is a relative coordinate of the light irradiation region in the coordinate system corresponding to the normalized light fluence distribution.

The calculation is performed by the normalized light fluence distribution acquiring unit 32 when the measurement starts (e.g. at first pulsed light irradiation), and the calculated normalized light fluence distribution is repeatedly used during measurement. The data of the normalized light fluence distribution does not change as long as the irradiating light to be used and the measurement target object are the same. In other words, by using the normalized light fluence distribution, the light fluence distribution inside the object can be acquired without operating the light fluence distribution from scratch each time the pulsed light is radiated.

Here the normalized light fluence corresponding to each position of the light absorbers A to C in states 1 to 3 is expressed as follows.

$$\Phi 1N(rA)=\Phi N(FS(rA,SP1))=0.5 \text{ J/m}^2, \Phi 1N(rB)=\Phi N(FS(rB,SP1))=0.03 \text{ J/m}^2, \Phi 1N(rC)=\Phi N(FS(rC,SP1))=0\text{J/m}^2$$

$$\Phi 2N(rA)=\Phi N(FS(rA,SP2))=0 \text{ J/m}^2, \Phi 2N(rB)=\Phi N(FS(rB,SP2))=5 \text{ J/m}^2, \Phi 2N(rC)=\Phi N(FS(rC,SP2))=0\text{J/m}^2$$

$$\Phi 3N(rA)=\Phi N(FS(rA,SP3))=0 \text{ J/m}^2, \Phi 3N(rB)=\Phi N(FS(rB,SP3))=0.05 \text{ J/m}^2, \Phi 3N(rC)=\Phi N(FS(rC,SP3))=0.25 \text{ J/m}^2$$

Here $\Phi N$ is the normalized light fluence distribution, and S1, S2 and S3 are positional coordinates of the irradiation region. FS is a function to convert the absolute coordinates rA, rB and rC of the absorbers and the positional coordinates SP1, SP2 and SP3 of the light irradiation region into the coordinate system of the normalized light fluence distribution. In other words, the function FS is a function to convert the normalized light fluence value in the coordinate system rr, corresponding to the normalized light fluence distribution, into the normalized light fluence value in the coordinate system corresponding to the irradiation region.

The light fluence distribution inside the object can be acquired by multiplying the acquired normalized light fluence by the total light intensity of the actual irradiating light. In this embodiment, the object information calculation unit 33 multiplies the normalized light fluence distribution ΦN(rr) by the light intensity E of the irradiating light, and calculates the absorption coefficient using the acquired light fluence distribution and the detection signal. The light intensity E of the irradiating light may be acquired by measuring the pulsed light emitted from the light irradiating unit 10, or may be estimated based on the information acquired from the light source.

If the light intensity of the irradiating light in each state is E1, E2 and E3, then the absorption coefficient can be calculated as follows.

$$\mu i(rA)=R(S1(rA),S2(rA),S3(rA))/\{(\Phi 1N(rA)\times E1+\Phi 2N(rA)\times E2+\Phi 3N(rA)\times E3)/3\} \quad \text{Expression (10)}$$

$$\mu i(rB)=R(S1(rB),S2(rB),S3(rB))/\{(\Phi 1N(rB)\times E1+\Phi 2i(rB)\times E2+\Phi 3i(rB)\times E3)/3\} \quad \text{Expression (11)}$$

$$\mu i(rC)=R(S1(rC),S2(rC),S3(rC))/\{(\Phi 1N(rC)\times E1+\Phi 2i(rC)\times E2+\Phi 3i(rA)\times E3)/3\} \quad \text{Expression (12)}$$

In Expression (10), Expression (11) and Expression (12), the normalized light fluence is multiplied by the light intensity E of the irradiating light, but the same result is acquired after operation by dividing the detected signal by the light intensity E of the irradiating light, as shown in Expression (13), Expression (14) and Expression (15).

$$\mu i(rA)=R(S1(rA)/E1,S2(rA)/E2,S3(rA)/E3)/\{(\Phi 1N(rA)+\Phi 2N(rA)+\Phi 3N(rA))/3\} \quad \text{Expression (13)}$$

$$\mu i(rB)=R(S1(rB)/E1,S2(rB)/E2,S3(rB)/E3)/\{(\Phi 1N(rB)+\Phi 2i(rB)+\Phi 3i(rB))/3\} \quad \text{Expression (14)}$$

$$\mu i(rC)=R(S1(rC)/E1,S2(rC)/E2,S3(rC)/E3)/\{(\Phi 1N(rC)+\Phi 2i(rC)+\Phi 3i(rC))/3\} \quad \text{Expression (15)}$$

Then the absorption coefficient of each light absorber is calculated using the above mentioned values. If the above mentioned values are applied to Expression (10), Expression (11) and Expression (12), the absorption coefficients become as follows.

$$\mu i(rA)=\{(7500+3+0.105)/3\}/\{(0.5\times 100+0\times 125+0\times 80)/3\}=150.0621/m$$

$$\mu i(rB)=\{(225+75000+300)/3\}/\{(0\times 100+4\times 125+0\times 80)/3\}=151.05/m$$

$$\mu i(rC)=\{(0.45+4.5+3000)/3\}/\{(0\times 100+0\times 125+0.25\times 80)/3\}=150.02/m$$

In other words, the absorption coefficient can be calculated at a 1% or less error from the true value 150/m.

Further, the method of calculating the initial sound pressure distribution is improved, and the absorption coefficient of each light absorber is calculated assuming that the sound pressure in a region, other than the light fluence distribution calculation region, is 0, then the result will be as follows.

$$\mu i(rA)=\{(7500+0+0)/3\}/\{(0.5\times 100+0\times 125+0\times 80)/3\}=150/m$$

$$\mu i(rB)=\{(0+75000+0)/3\}/\{0\times 100+4\times 125+0\times 80)/3\}=150/m$$

$$\mu i(rC)=\{(0+0+3000)/3\}/\{(0\times 100+0\times 125+0.25\times 80)/3\}=150/m$$

As described above, according to this embodiment, the light fluence distribution is calculated using the normalized light fluence distribution which is calculated in advance, whereby it is unnecessary to calculate the light fluence distribution for each irradiation of the irradiating light using a costly method. For example, in the case of FIG. 2A to FIG. 2C, it is unnecessary to calculate the light fluence distribution respectively in state 1, state 2 and state 3, hence the speed of calculating the light fluence distribution can be improved by about three times. In this example, the three states were used as an example, hence the calculation time can be shortened even more as the number of states increases.

In this embodiment, an example of calculating the normalized light fluence distribution based on the assumption that the profile of the irradiating light is constant in each pulsed light. If it is assumed that not only the profile of the irradiating light, but also the total light intensity of the irradiating light is constant in each pulsed light, then the calculated light fluence distribution itself may be acquired as the normalized light fluence distribution, as in the case of prior art. In other words, the normalized light fluence distribution acquiring unit 32 may calculate the light fluence distribution based on the profile of the irradiating light and the optical coefficient of the object, and store the calculated light fluence distribution in the memory 34 as the normalized light fluence distribution. In this case, the object information calculation unit 33 may handle the normalized light fluence distribution as the light fluence distribution when each an object is irradiated with pulsed light.

If the irradiation position of each pulsed light is different, the light fluence distribution changes in relation to the irradiation position, as shown in FIG. 2A to FIG. 2C, hence in this case, the light fluence distribution Φ(r) inside the object is calculated using each position r inside the object, and a function FS(r, SP) that converts the positional coordinates SP of the irradiation region into the coordinate system of the normalized light fluence distribution ΦN(R).

Light fluence distribution Φ(r)=ΦN(FS(r,SP))

<Processing Flow Chart>

Figure 3:
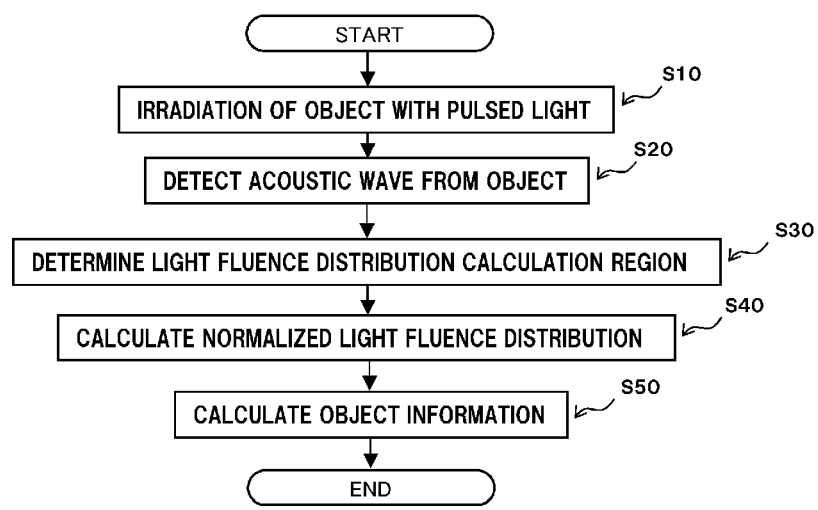
FIG. 3 is a flow chart depicting the processing of the photoacoustic measuring apparatus according to Embodiment 1.

A processing flow chart to implement the above described processing will be described. FIG. 3 is a flow chart of the processing executed by the photoacoustic measuring apparatus according to this embodiment.

First in step S10, the object is irradiated with the pulsed light (irradiating light) from the light irradiating unit 10.

Then in step S20, the acoustic wave generated from the object is detected by the acoustic wave detection unit 20, is converted into an electric signal, and is stored in the memory 34 of the signal processing unit 30. If the irradiating light is radiated for a plurality of times, the irradiation of the pulsed light and the signal acquisition (steps S1 and S2) are repeatedly executed. For this, the timing of the irradiation of the irradiating light and the timing of the detection of the acoustic wave must be synchronized.

Then in step S30, the light fluence distribution calculation region determination unit 31 determines a target region to calculate the light fluence distribution (light fluence distribution calculation region). In this step, as mentioned above, when the light enters the object a region where the irradiating light fluence is sufficiently strong is determined based on: the light fluence distribution of the irradiating light on the surface of the object; the shape of the object; and the average absorption coefficient and average scattering coefficient of the object, and regards this region as the light fluence distribution calculation region. The light fluence distribution calculation region may be set based on the spatial sensitivity distribution acquired from directivity, the band sensitivity or the like of the probe, and the SNR may be calculated from the absorption coefficient and the size of the observation target light absorber, and the light fluence distribution calculation region may be set based on the comparison result between this SNR and a threshold.

Then in step S40, the normalized light fluence distribution acquiring unit 32 calculates the normalized light fluence distribution in the light fluence distribution calculation region based on the normalized irradiating light fluence distribution O', and the average absorption coefficient and the average scattering coefficient of the object.

Then in step S50, the object information calculation unit 33 calculates the object information. In concrete terms, the normalized light fluence distribution calculated in step S40 is multiplied by the total light intensity of the irradiating light, and the result is acquired as the light fluence distribution. Then the object information calculation unit 33 acquires the initial sound pressure distribution by applying an arbitrary reconstruction method to the detection signal, and acquires the absorption coefficient distribution based on Expression (1). In this example, the absorption coefficient distribution is acquired, but a concentration distribution of an arbitrary component (e.g. oxygen saturation degree) may be calculated by acquiring the absorption coefficient distribution corresponding to different wavelengths respectively.

The calculated absorption coefficient distribution is presented to the operator of the apparatus via a display device (not illustrated).

In this embodiment, the normalized irradiating light fluence distribution and the normalized light fluence distribution are calculated when the measurement is started, and the result is used for the subsequent measurement, but if the characteristics of the irradiating light and the object are known in advance, the normalized irradiating light fluence distribution and the normalized light fluence distribution may be stored in advance and used. Further, a plurality of normalized irradiating light fluence distributions and normalized light fluence distributions corresponding to different irradiating light beams and objects may be stored in advance and used selectively.

The normalized irradiating light fluence distribution is acquired by measuring, using a camera or the like, the two-dimensional profile of the irradiating light in a position where the irradiating light enters the object, and normalizing such that the total pixels of the two-dimensional profile becomes 1. The normalized light fluence distribution is calculated from the normalized irradiating light fluence distribution using a diffusion equation or a transfer equation.

To calculate the normalized light fluence distribution, the light fluence distribution may be calculated first by using a diffusion equation or a transfer equation, then the acquired result may be normalized. For example, in the first pulsed light irradiation, the light fluence distribution is acquired using a conventional method, then this light fluence distribution is normalized and held, and is then used in the second or later irradiation.

Any method can be used if the light fluence distribution inside the object can be calculated using the normalized light fluence distribution.

Furthermore, the average of the sum of light intensity distribution information may be calculated using the average of the sum of irradiating light fluence distributions, which is data that sums up the irradiating light fluence distribution at each irradiation, calculated from the product of the normalized irradiating light fluence distribution and the irradiating light intensity. This method will be described with reference to FIG. 13A to FIG. 13C.

FIG. 13A is a diagram depicting the normalized irradiating light fluence distribution ILD_N(rr). As illustrated in FIG. 2A to FIG. 2C, if measurement is performed at three locations in state 1, state 2 and state 3, the average of sum of ILD of the irradiating light fluence distribution for three times of irradiation, as shown in FIG. 13B, is given by the following expression:

$$ILD(r)=(ILD\_N(FS(r,SP1))\times E1+ILD\_N(FS(r,SP2))\times E2+ILD\_N(FS(r,SP3))\times E3)/3$$

From the average of sum of irradiating light fluence distribution ILD(r) determined like this, the light fluence distribution $\Phi(r)$ can be calculated using a diffusion equation or a transfer equation (FIG. 13C).

To calculate the normalized light fluence distribution, the light fluence distribution may be calculated first by using a diffusion equation or a transfar equation, then the acquired result may be normalized. For example, in the first pulsed light irradiation, the light fluence distribution is acquired using a conventional method, then this light fluence distribution is normalized and held, and is then used in the second or later irradiation.

Any method can be used if the light fluence distribution inside the object can be calculated using the normalized light fluence distribution.

Furthermore, average of sum of light intensity distribution may be calculated using the average of sum of irradiating light fluence distribution, which is data that sums up the irradiating light fluence distribution at each irradiation, calculated from the product of the normalized irradiating light fluence distribution and the irradiating light intensity. This method will be described with reference to FIG. 13A to FIG. 13C.

FIG. 13A is a diagram depicting the normalized irradiating light fluence distribution ILD_N(rr). As illustrated in FIG. 2A to FIG. 2C, if measurement is performed at three locations in state 1, state 2 and state 3, the average of sum of ILD of the irradiating light fluence distribution for three times of irradiation, as shown in FIG. 13B, is given by the following expression.

$$ILD(r)=(ILD\_N(FS(r,SP1))\times E1+ILD\_N(FS(r,SP2))\times E2+ILD\_N(FS(r,SP3))\times E3)/3$$

From the average of sum of irradiating light fluence distribution ILD(r) determined like this, the light fluence distribution $\Phi(r)$ can be calculated using a diffusion equation or a transfar equation (FIG. 13C).

Embodiment 2

A photoacoustic measuring apparatus according to Embodiment 2 is an apparatus configured to compress and hold a breast of a subject using two holding plates, and image the distribution of the oxygen saturation degree in the breast.

Figure 4:
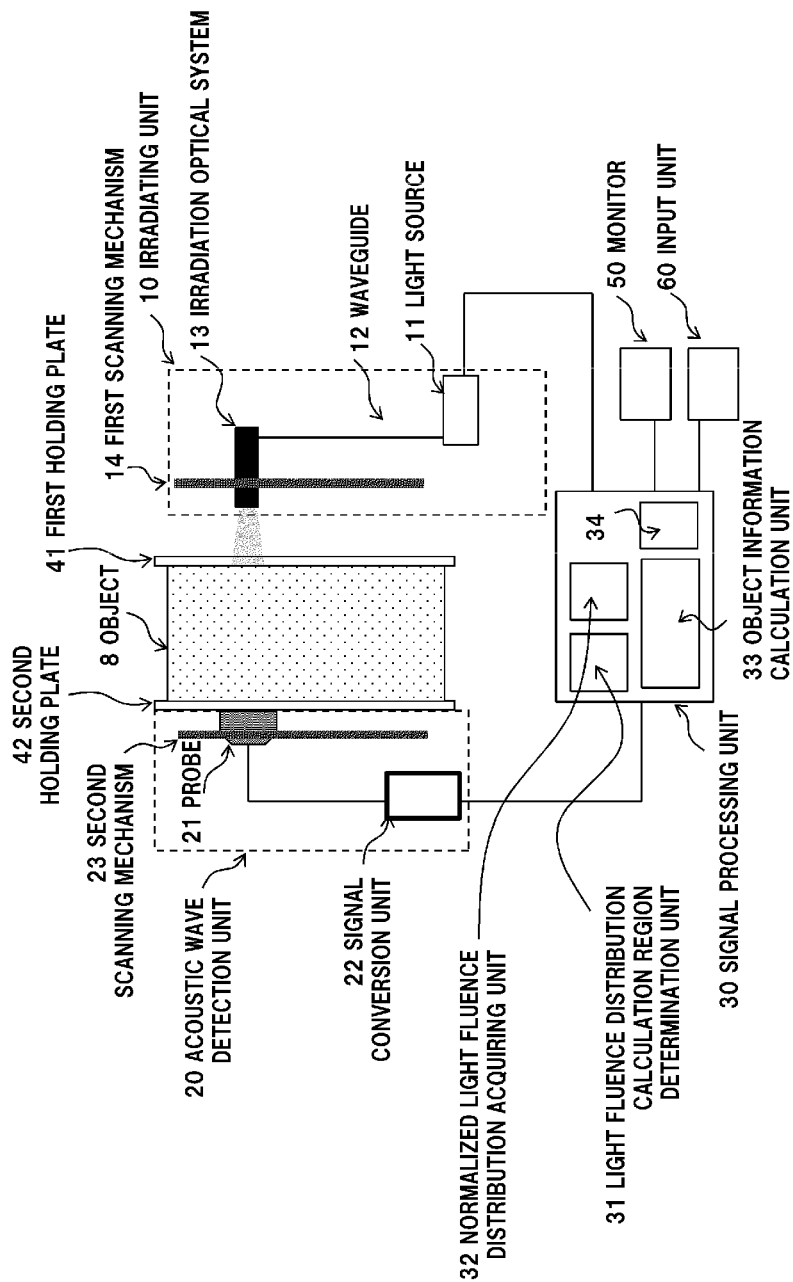
FIG. 4 is a system block diagram of a photoacoustic measuring apparatus according to Embodiment 2.

FIG. 4 is a system block diagram of the photoacoustic measuring apparatus according to Embodiment 2. A composing element the same as Embodiment 1 is denoted with a same reference numeral, for which description is omitted.

The photoacoustic measuring apparatus according to Embodiment 2 has a light irradiating unit 10 constituted by a light source 11, a waveguide 12, an irradiation optical system 13, and a first scanning mechanism 14.

The light source 11 is an Nd:YAG-excited Ti-sa laser, which can radiate pulsed light having a 30 nanosecond pulse width at 10 Hz. The light source 11 can switch the wavelength of the pulsed light to be emitted between two types: 756 nm and 797 nm.

The waveguide 12 is an optical fiber bundle serving as a unit that guides the pulsed light emitted from the light source 11 to the irradiation optical system 13.

The irradiation optical system 13 is a unit that irradiates the object with the irradiating light. In concrete terms, the irradiation optical system 13 is constituted by a magnifying lens and a diffusion plate, so that the object 2 can be irradiated with the pulsed light emitted from the waveguide 12 at a predetermined irradiation density.

The first scanning mechanism 14 is a scanning mechanism to move the irradiation optical system 13 horizontally along a rail using a pulse motor. The rail is disposed parallel with a first holding plate 14, so that the irradiation optical system 13 can be moved in two-dimensional directions (vertical direction and depth direction in FIG. 4). The first scanning mechanism includes a mechanism to detect the position of the irradiation optical system 13 (e.g. photodetector to detect an irradiating light), and sends the detected position to a signal processing unit 30. Information on energy of the irradiating light emitted from the light source 11 is also sent to the signal processing unit 30. Thereby the total light intensity per pulse can be calculated.

In this embodiment, the object is held between a first holding plate 41 and a second holding plate 42, which are plane parallel plates. Thereby the shape of the surface of the object at a position contacting the holding plates is dictated by the shape of the holding plate(s). The first holding plate 41 and the second holding plate 42 are made from polymethylpentene, which is transmissive to both light and acoustic waves.

The first holding plate 41 and the second holding plate 42 are configured to be movable, so that the distance between the holding plates can change. One or both of the holding plates may be movable. The distance between the first holding plate 41 and the second holding plate 42 is sent to the calculation processing unit 4, and is used as the object shape information.

The photoacoustic measuring apparatus according to Embodiment 2 also has an acoustic wave detection unit 20 constituted by a probe 21, a signal conversion unit 22, and a second scanning mechanism 23.

The probe 21 is a two-dimensionally arrayed probe completely formed of 20×30 cMUT elements, each element is 1×1 mm in size, with a 2 MHz central frequency band and 100% of bandwidth. The space between the probe 21 and the second holding plate 42 is filled with castor oil to match acoustic impedance.

The signal conversion unit 22 is a unit to amplify the detection signal acquired by the probe 21, and convert the electric signal from an analog signal into a digital signal. The converted signal is sent to the signal processing unit 30.

The second scanning mechanism 23 is a scanning mechanism to horizontally move the probe 21 along the rail using a pulse motor. The rail is disposed parallel with the second holding plate 42, and allows the probe 21 to move in two-dimensional directions (vertical direction and depth direction in FIG. 4). The second scanning mechanism 23 is interlocked with the first scanning mechanism 14. In other words, the second scanning mechanism 23 is controlled so that the probe 21 is located on the rear side of the position where the object is irradiated with the irradiating light.

The signal processing unit 30 according to this embodiment includes: a light fluence distribution calculation region determination unit 31; a normalized light fluence distribution acquiring unit 32; and an object information calculation unit 33, just like Embodiment 1. In this embodiment, the signal processing unit 30 is a workstation, and the light fluence distribution calculation region determination unit 31, the normalized light fluence distribution acquiring unit 32, and the object information calculation unit 33 are programs that run on this workstation.

In Embodiment 2, the signal processing unit 30 acquires information on the energy of the irradiating light emitted from the light source 11, converts this information into the total light intensity of the pulsed light radiated to the object, multiplies the acquired normalized light fluence distribution by this total light intensity of pulsed light, and acquires the light fluence distribution used for the calculation of the absorption coefficient.

The signal processing unit 30 acquires the average absorption coefficient and the average scattering coefficient of the object 2 via an input unit 60, and these coefficients are used when the normalized light fluence distribution acquiring unit 32 calculates the light fluence distribution.

Further, the signal processing unit 30 acquires the distance between the first holding plate 41 and the second holding plate 42, and acquires the light fluence distribution assuming that the entire object 2 exists between these two holding plates.

In Embodiment 1, the absorption coefficient distribution is acquired using only one wavelength, but the signal processing unit 30, according to Embodiment 2, acquires the absorption distribution using two wavelengths respectively, and calculates the distribution of the oxygen saturation degree inside the object using Expression (16).

$$StO = (\mu i_{756}(r) \times \varepsilon HbR_{756} - \mu i_{797}(r) \times \varepsilon HbR_{797})/(\mu i_{756}(r) \times (\varepsilon HbR_{756} - \varepsilon HbO_{756}) - \mu i_{797}(r) \times (\varepsilon HbR_{797} - \varepsilon HbO_{797}))$$ Expression (16)

Here $\varepsilon HbR_{756}$ is an absorption coefficient of the deoxyhemoglobin at a 756 nm wavelength, and $\varepsilon HbR_{797}$ is an absorption coefficient of the deoxyhemoglobin at a 797 nm wavelength. $\varepsilon HbO_{756}$ is an absorption coefficient of the oxyhemoglobin at a 756 nm wavelength, and $\varepsilon HbO_{797}$ is an absorption coefficient of the oxyhemoglobin at a 797 nm wavelength. $\mu i_{756}(r)$ is an absorption coefficient distribution acquired by the measurement using the pulsed light of which wavelength is 756 nm, and $\mu i_{797}(r)$ is an absorption coefficient distribution acquired by the measurement using the pulsed light of which wavelength is 797 nm.

Figure 5:
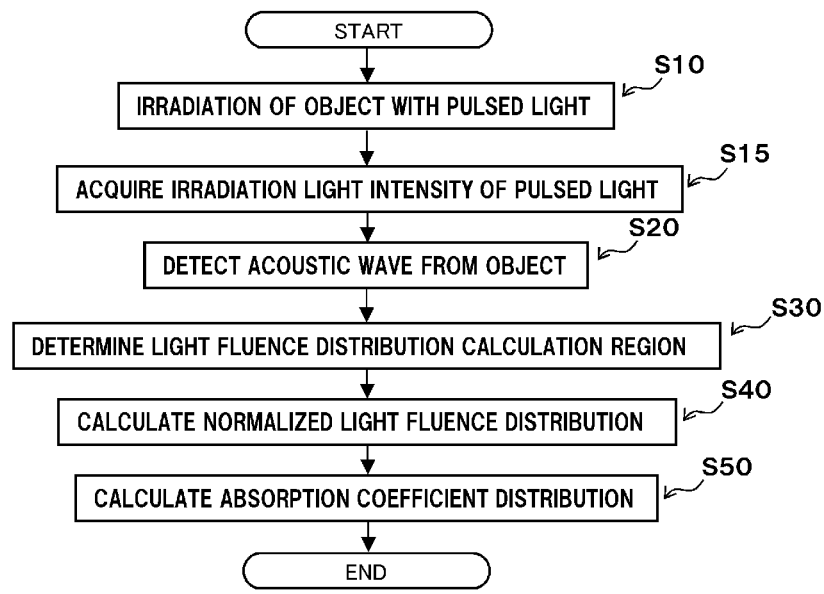
FIG. 5 is a flow chart depicting the processing of the photoacoustic measuring apparatus according to Embodiment 2.

FIG. 5 is a flow chart depicting the processing executed by the signal processing unit 30 according to Embodiment 2.

The difference of the flow chart in FIG. 5 from the first embodiment (FIG. 3) is that a step of acquiring the light fluence of the pulsed light with which the object is irradiated (step S15) is added after step S10 is completed.

In step S15, the total light intensity of the irradiating light at each position is calculated using the input energy to the light source and a coefficient provided in advance (coefficient to convert this energy into a total light intensity of the irradiating light). The calculated light intensity is used for converting the normalized light fluence distribution into an actual light fluence distribution in step S50.

Moreover, in Embodiment 2, the processing in steps S10 to S50 is executed for each wavelength, and the oxygen saturation degree is calculated based on the acquired plurality of absorption coefficient distributions. The calculated oxygen saturation degree is presented to the operator of the apparatus via a monitor 50.

In the photoacoustic measuring apparatus according to Embodiment 2, the shape of the object is specified by the holding plate, and the surface of the object is irradiated with the irradiating light in an approximately same pattern. In other words, if one normalized irradiating light fluence distribution is determined in advance, this distribution can be used for all irradiation.

The average absorption coefficient and the average scattering coefficient may be inputted by an operator, or may be values that are measured and stored in advance.

Embodiment 3

The photoacoustic measuring apparatus according to Embodiment 3 is an apparatus to image the absorption coefficient distribution in a breast, is a hand-held apparatus where a probe 21 and an irradiation optical system 13 are housed in a casing 80, and is configured to contact an object and perform measurement.

Figure 6:
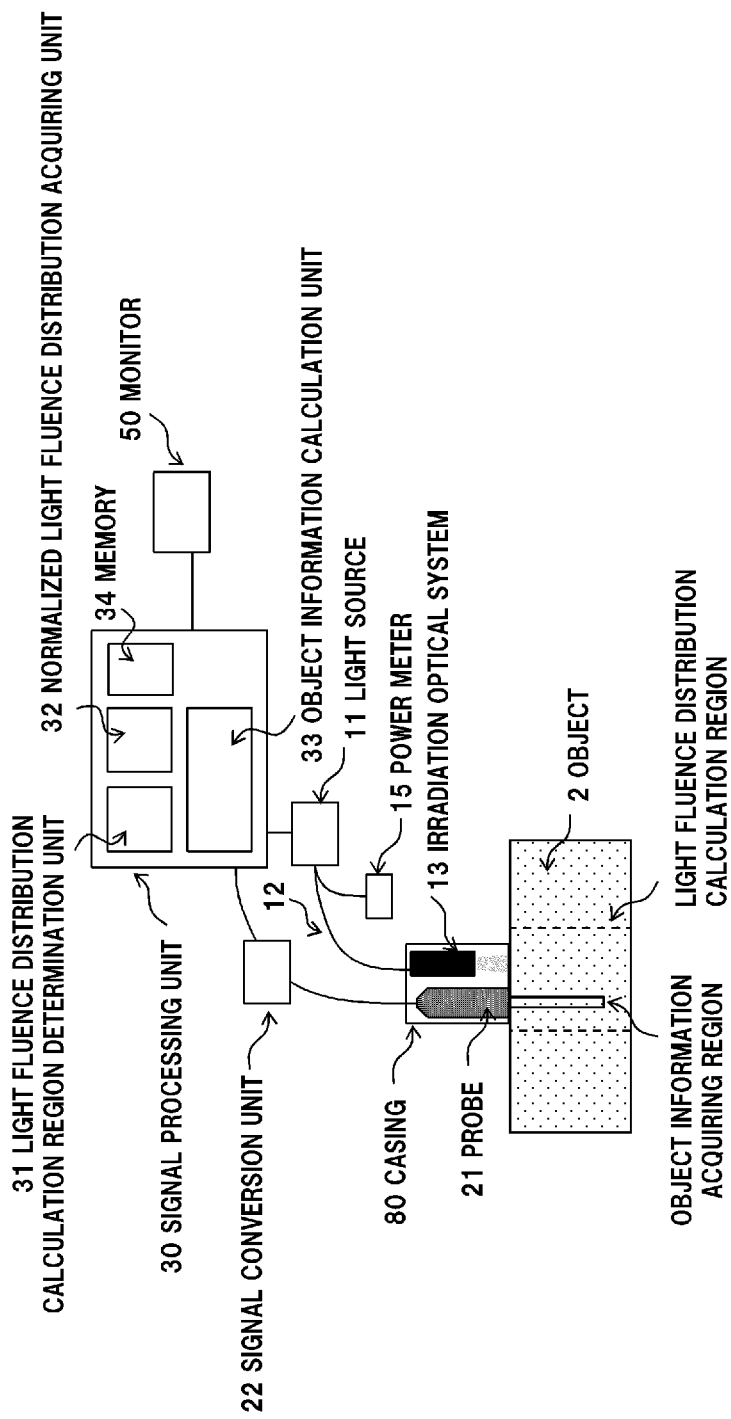
FIG. 6 is a system block diagram of a photoacoustic measuring apparatus according to Embodiment 3.

FIG. 6 is a system block diagram of the photoacoustic measuring apparatus according to Embodiment 3. A composing element the same as Embodiment 1 is denoted with a same reference numeral, for which description is omitted.

The photoacoustic measuring apparatus according to Embodiment 3 has a light irradiating unit 10 constituted by a light source 11, a waveguide 12, an irradiation optical system 13, and a power meter 15.

The light source 11 is an alexandrite laser, and can radiate pulsed light having a 100 nanosecond pulse width at 20 Hz in a 700 nm to 800 nm wavelength range.

The waveguide 12 is an optical fiber bundle that guides the pulsed light emitted from the light source 11 to the irradiation optical system 13. The waveguide 12 is also a unit to branch a part of the pulsed light emitted from the light source, and guide the branched pulsed light to the power meter 15.

The irradiation optical system 13 is a unit that irradiates the object with the irradiating light. In concrete terms, the irradiation optical system 13 is constituted by a magnifying lens and a diffusion plate, so that the object 2 can be irradiated with the pulsed light emitted from the waveguide 12 at a predetermined irradiation density.

The power meter 15 is a unit (an irradiating light intensity acquiring unit) that detects a light intensity of a part of the pulsed light emitted from the light source, and measures the light intensity. The detection result is sent to a signal processing unit 30.

The photoacoustic measuring apparatus according to Embodiment 3 also has an acoustic wave detection unit 20 constituted by a probe 21 and a signal conversion unit 22. The probe 21 is a one-dimensional array probe in which 20 piezoelectric elements (1 mm size) are arrayed in the depth direction in FIG. 6, to which an acoustic lens is added. The probe 21 is configured to detect only a signal on the two-dimensional surface constituted by the array direction of the elements (depth direction in FIG. 6) and the vertical direction in FIG. 6.

The signal conversion unit 22 is a unit to amplify the detection signal acquired by the probe 21, and convert an electric signal from an analog signal into a digital signal. The converted signal is sent to the signal processing unit 30.

In Embodiment 3 as well, the signal processing unit 30 includes: a light fluence distribution calculation region determination unit 31; a normalized light fluence distribution acquiring unit 32; and an object information calculation unit 33.

In this embodiment, the acoustic elements of the probe 21 are one-dimensionally arrayed, hence the acoustic wave can be detected only in the front face region of the probe (hereafter called an "object information acquiring region"). Therefore processing can be performed if the light fluence distribution is acquired only for the object information acquiring region.

However the light fluence distribution must be calculated for a region that includes the position where the surface of the object is irradiated with the irradiating light. Further, a region where a boundary condition at the boundary of the light fluence distribution calculation region considerably influences the calculated light fluence is a region several mm from the boundary. Therefore in this embodiment, a region slightly larger than the object information acquiring region is set as the light fluence distribution calculation region. In concrete terms, a region 10 mm larger than the object information acquiring region is set as the light fluence distribution calculation region.

In this embodiment, just like Embodiment 2, the normalized light fluence distribution acquiring unit 32 calculates the light fluence distribution (normalized light fluence distribution) in the light fluence distribution calculation region when the normalized light fluence distribution acquiring unit 32 normalizes the total light intensity of the irradiating light.

Now the processing performed by the object information calculation unit 33 according to this embodiment will be described with reference to FIG. 6. In this embodiment, the pulsed light is radiated for a plurality of times without changing the positions of the irradiation optical system 13 and the probe 21.

For example, if the pulsed light is radiated three times and a state of each irradiation is referred to as state 1, state 2 and state 3, the positional relationship of the irradiation optical system 13 and the probe 21 does not change in each state, as illustrated in FIG. 7A to FIG. 7C.

If the light intensity of the irradiating light in each state is E1, E2 and E3, then the absorption coefficient of the light absorber 3 at the position r is calculated as follows using Expression (10).

$$\mu i(r)=R(S1(r),S1(r),S3(r))/\{(\Phi N(r) \times E1+\Phi N(r) \times E2+\Phi N(r) \times E3)/3\}$$

Or the absorption coefficient is calculated as follows using Expression (13).

$$\mu i(r)=R(S1(r)/E1,S2(r)/E2,S3(r)/E3)/\{(\Phi N(r)+\Phi N(r)+\Phi N(r))/3\}$$

The normalized light fluence distribution acquiring unit 32 according to this embodiment calculates the normalized light fluence distribution assuming that the object extends infinitely from the surface contacting the casing in the depth direction. For the average absorption coefficient and the average scattering coefficient of the object 2, the average values of the statistical data of a human breast are stored in advance and used.

The flow chart of the processing that the signal processing unit 30 executes according to Embodiment 3 is the same as Embodiment 2 (FIG. 5), except that a step of calculating the total light intensity of the irradiating light based on the light intensity of the pulsed light acquired by the power meter 15 is added. In concrete terms, in step S15, the light intensity of the pulsed light acquired by the power meter 15 is multiplied by a coefficient (coefficient to convert the measured light intensity into the total light intensity of the irradiating light), which is provided in advance, so as to calculate the total light intensity of the irradiating light at each position. The calculated light intensity is used to convert the normalized light fluence distribution into the actual light fluence distribution in step S50.

Another difference is that the light fluence calculation region is set by the above mentioned method in the processing in step S30. The other steps are the same as described in Embodiment 2.

In Embodiment 3, just like Embodiment 2, the light fluence by which the initial sound pressure R (S1(r), S2(r), S3(r)) is divided may be calculated after calculating the average of sum of irradiating light fluence distribution ILD(r) first, using the normalized irradiating light fluence distribution ILD_N(rr) and the irradiating light intensity.

Embodiment 4

The photoacoustic measuring apparatus according to Embodiment 4 is an apparatus to image a relative hemoglobin concentration distribution of a breast, where measurement is performed using a bowl-shaped probe.

Figure 8:
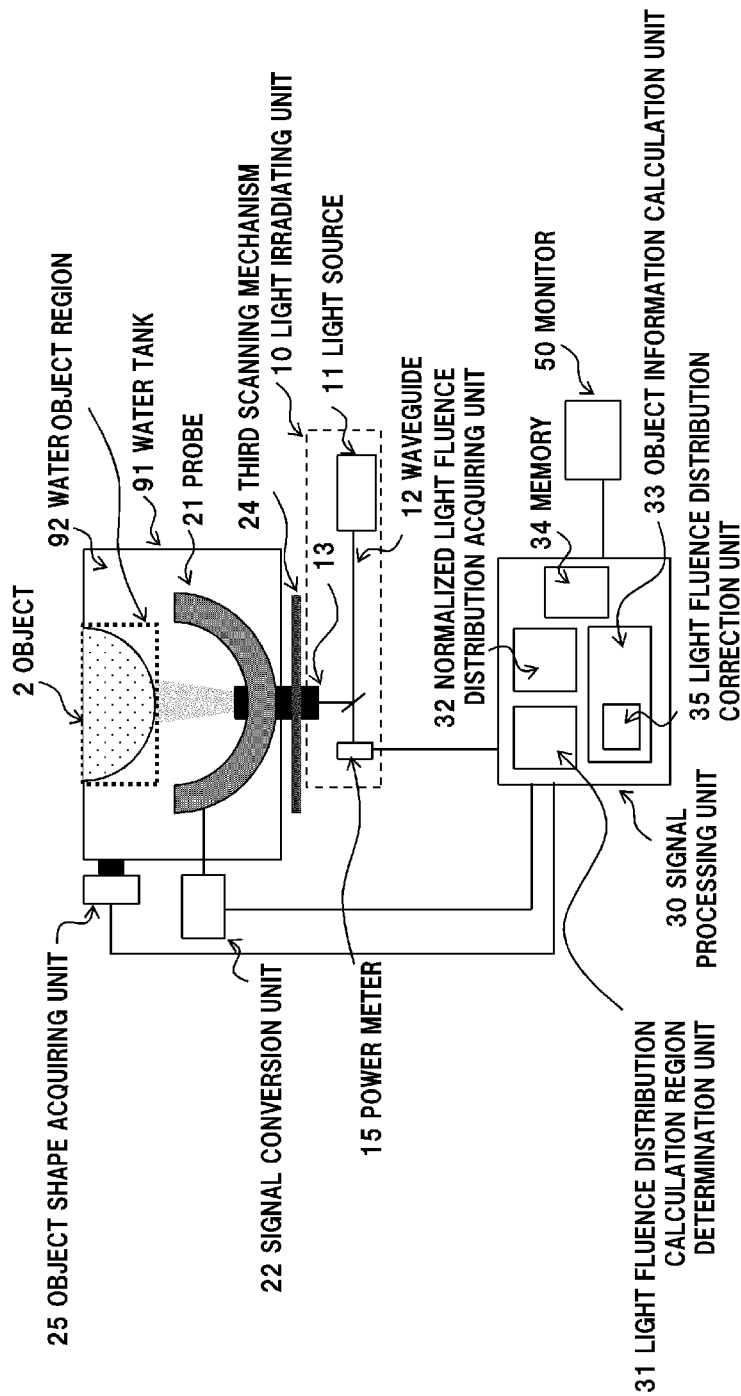
FIG. 8 is a system block diagram of a photoacoustic measuring apparatus according to Embodiment 4.

FIG. 8 is a system block diagram of the photoacoustic measuring apparatus according to Embodiment 4. A composing element the same as Embodiment 1 is denoted with a same reference numeral, for which description is omitted.

The photoacoustic measuring apparatus according to Embodiment 4 has a light irradiating unit 10 constituted by a light source 11, a waveguide 12, an irradiation optical system 13 and a power meter 15.

The light source 11 is an alexandrite laser, and can radiate pulsed light having a 100 nanosecond pulse width at 20 Hz with a 797 nm wavelength.

The waveguide 12 is an arm with a reflection mirror to spatially propagate the laser light, and is a unit to guide the pulsed light emitted from the light source 11 to the irradiation optical system 13. The waveguide 12 is also a unit to branch a part of the pulsed light emitted from the light source, and guide the branched pulsed light to the power meter 15.

The irradiation optical system 13 is a unit that irradiates the object with the irradiating light. In concrete terms, the irradiation optical system 13 is constituted by a magnifying lens and a diffusion plate, so that the object 2 can be irradiated with the pulsed light emitted from the waveguide 12 at a predetermined irradiation density.

The power meter 15 is a unit to detect a light intensity of a part of the pulsed light emitted from the light source, and measure the light intensity. The detection result is sent to a signal processing unit 30.

The photoacoustic measuring apparatus according to Embodiment 4 also has an acoustic wave detection unit 20 constituted by a probe 21 and a signal conversion unit 22.

The probe 21 is configured such that 512 piezoelectric elements, that face the center of a sphere, are arranged in a Fibonacci array on the inner surface of a hemispherical bowl type holding member.

The signal conversion unit 22 is a unit to amplify the detection signal acquired by the probe 21, and convert an electric signal from an analog signal into a digital signal. The converted signal is sent to the signal processing unit 30.

In the photoacoustic measuring apparatus according to Embodiment 4, the probe 21 and the irradiation optical system 13 are integrated, and as illustrated in FIG. 8, the pulsed light is radiated toward the center of the sphere from the bottom surface of the bowl type probe. The probe 21 and the irradiation optical system 13 are disposed in a water tank 91, and the water tank 91 is filled with water 92, so as to match acoustic impedance with the object 2. The relative positions of the probe 21 and the irradiation optical system 13, with respect to the object, can be changed by a third scanning mechanism 24.

In Embodiment 4, the irradiation optical system 13 does not contact with the object, hence if the irradiated surface of the object changes, the light fluence distribution inside the object changes. In other words, the normalized light fluence distribution cannot be calculated correctly if the above mentioned method is used.

Therefore in this embodiment, the shape of the object is measured using an object shape acquiring unit 25, and the normalized light fluence distribution is corrected using the measurement result. The object shape acquiring unit 25 may use any method if the shape of the object can be acquired. For example, cameras may be set in a plurality of locations so that the shape is calculated based on the projected shape of the object. A "time of flight" camera may be used, or patterns may be projected by a projector and imaged by a camera, whereby the shape is acquired. Moreover, ultrasonic waves may be transmitted/received so that the shape is extracted based on the difference of acoustic impedance between the object and water, or the shape may be extracted based on the signal outputted by the absorption of light on the surface of the object utilizing the photoacoustic characteristics.

A method for correcting the normalized light fluence distribution using the acquired shape will be described later.

In Embodiment 4 as well, the signal processing unit 30 includes: a light fluence distribution calculation region determination unit 31; a normalized light fluence distribution acquiring unit 32; and an object information calculation unit 33. The signal processing unit 30 also includes a light fluence distribution correction unit 35 to correct the normalized light fluence distribution in accordance with the shape of the object.

The light fluence distribution calculation region determination unit 31 determines an object region separately from the light fluence distribution calculation region. The object region is a region surrounded by a rectangular parallelepiped shape so that the entire shape of the object can be included. It is preferable that the object region is filled with the object as much as possible, and has a surface through which the irradiating light can enter perpendicularly. In this embodiment, the object region is a rectangular parallelepiped region, which is 24 mm in the X axis direction, 24 mm in the Y axis direction, and 10 mm in the Z axis direction (X axis is the horizontal direction, Y axis is the depth direction, and Z axis is the vertical direction in FIG. 8).

The light fluence distribution calculation region determination unit 31 determines the light fluence distribution calculation region by the same method as Embodiment 2. In this embodiment, the size of the light fluence distribution calculation region is assumed to be 10 mm×10 mm×10 mm. Further, the normalized light fluence distribution acquiring unit 32 calculates the normalized light fluence distribution by the same method as Embodiment 2.

As mentioned above, in this embodiment, the probe and the irradiation optical system are not in contact with the object, hence the shape of the surface of the object, when the irradiating light enters the object, changes in each irradiation. In other words, the normalized light fluence distribution cannot be accurately calculated if the above mentioned method is used.

Therefore in this embodiment, the generated normalized light fluence distribution is corrected based on the shape of the object, and the light fluence distribution inside the object is estimated using the corrected normalized light fluence distribution.

FIG. 9A to FIG. 9C are diagrams depicting cases when the probe 21 and the irradiation optical system 13 are in different positions with respect to the object. Here the positional relationships shown in FIG. 9A, FIG. 9B and FIG. 9C are assumed to be state 1, state 2 and state 3 respectively.

In this embodiment, the light fluence distribution correction unit 35 corrects (transforms) the normalized light fluence distribution determined in the light fluence distribution calculation region based on the shape of the object. In other words, the light fluence distribution correction unit 35 corrects the coordinates of the normalized light fluence distribution so that the coordinates of the normalized light fluence distribution correspond to the coordinates of the outer shape of the object.

Figure 10E:
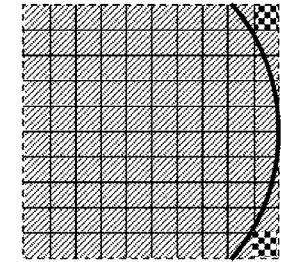
FIG. 10A to FIG. 10G are diagrams depicting a method for correcting a normalized light fluence distribution.
Figure 10F:
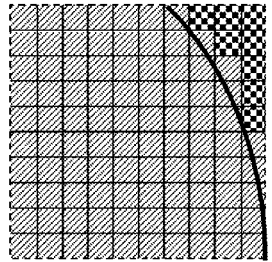
Figure 10G:
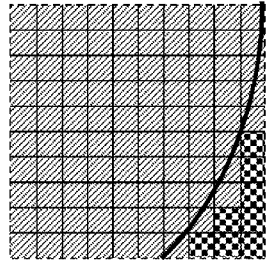
Figure 10B:
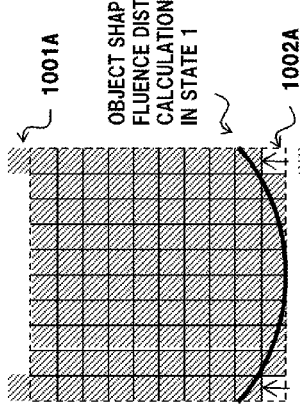
Figure 10C:
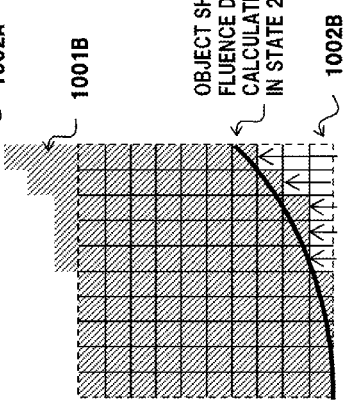
Figure 10D:
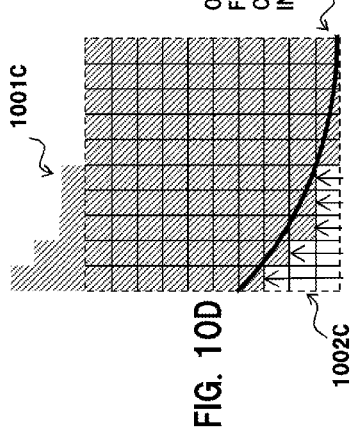
Figure 10A:
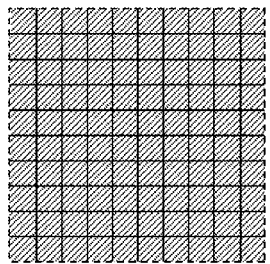
Figure 11:
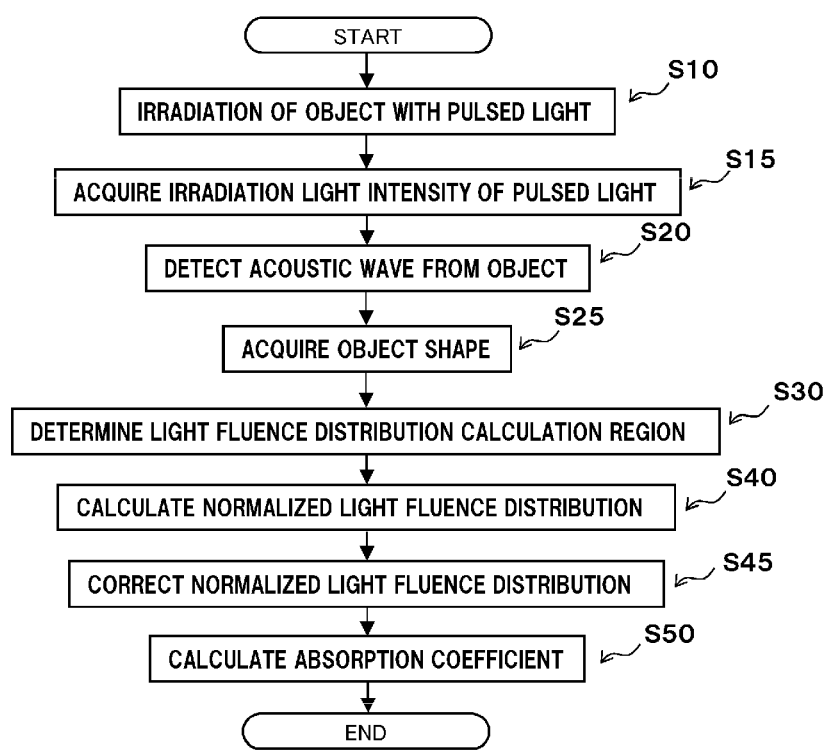
FIG. 11 is a flow chart depicting the processing of the photoacoustic measuring apparatus according to Embodiment 4.

As shown in FIG. 10A, the normalized light fluence distribution is divided into a 1 mm cubic grid parallel with the X axis, Y axis and Z axis. Then as shown in FIG. 10B, FIG. 10C and FIG. 10D, the normalized light fluence distribution divided into a 1 mm cubic grid is slid in 1 mm units in the Z direction, and is matched with the shape of the object in each state. At this time, the portions that spread from the light fluence distribution calculation region (indicated by 1001A, 1001B and 1001C) after being slid are deleted, and the maximum value of the normalized light fluence distribution is filled into the portions (reference numerals 1002A, 1002B and 1002C) of which no values exist after being slid.

By this processing, the corrected normalized light fluence distribution is acquired, as shown in FIG. 10E, FIG. 10F and FIG. 10G.

Then the object information calculation unit 33 calculates the absorption coefficient in the object using the corrected normalized light fluence distribution, instead of the normalized light fluence distribution in Embodiment 2, by the same method as Embodiment 2.

The flow chart of the processing executed by the signal processing unit 30 according to Embodiment 4 is the same as Embodiment 2 (FIG. 5), except that a step of measuring the shape of the object is added. In concrete terms, in step S25, the shape of the surface irradiated with the pulsed light is measured by the above mentioned method. The shape of the object is measured only when the shape or positioning of the object changed from the previous measurement.

The other difference from Embodiment 2 is that a step of correcting the normalized light fluence distribution in accordance with the shape of the object that exists in the light fluence distribution calculation region (step S45) is added. The correction method can be the above mentioned method of shifting the value corresponding to each grid in the irradiation direction of the irradiating light toward the depth direction of the object, for example. The correction may be performed by such a method as an affine transformation. The values that spread outside the light fluence distribution calculation region may be deleted. Further, the maximum value of the normalized light fluence distribution may be substituted for the grid of which values do not exist after being slid.

The other steps are the same as Embodiment 2.

Figure 12:
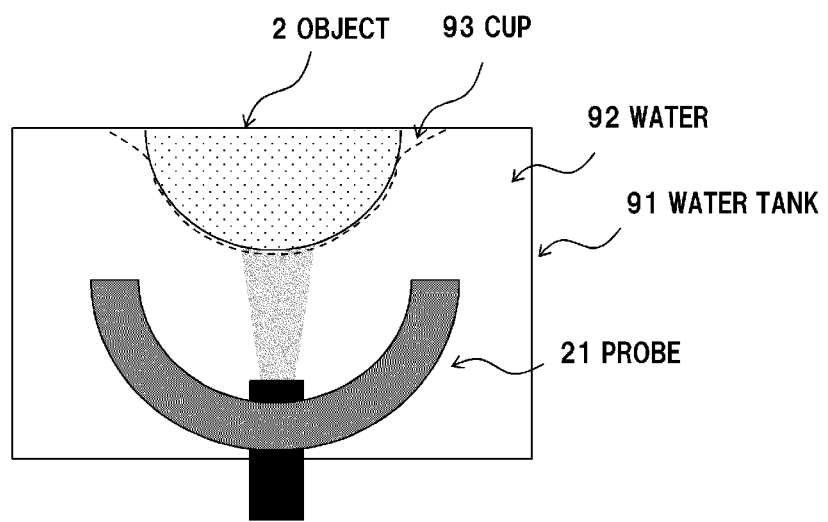
FIG. 12 is a diagram depicting a modification of Embodiment 4.

A member to specify the shape of an object may be disposed in a portion where an object is inserted. For example, a holding member, such as cup 93 shown in FIG. 12, which the object is pressed against and held during measurement, may be disposed. Thereby the shape of the irradiated surface becomes a predetermined shape, and measurement of the shape of the object can be omitted. The shape of the holding member may be stored in the object shape acquiring unit 25 in advance.

If the shape of the holding member is predetermined, it is unnecessary to correct the normalized light fluence distribution each time measurement is performed. For example, the corrected normalized light fluence distribution may be stored for each holding member to be used, and an appropriate corrected normalized light fluence distribution may be used.

Further, in Embodiment 4, the light fluence by which the initial sound pressure R(S1(r), S2(r), S3(r)) is divided may be calculated after calculating the average of sum of irradiating light fluence distribution ILD(r) first using the normalized irradiating light fluence distribution ILD_N(rr) and the irradiating light intensity, just like Embodiment 1, so as to match with the shape of the object, as shown in FIG. 10A to FIG. 10G.

(Modifications)

The description on each embodiment is an example, and the present invention can be carried out by appropriately changing or combining the above embodiments in a scope that does not depart from the true spirit of the invention.

For example, the present invention may be carried out as an object information acquiring apparatus that includes at least a part of the above mentioned units. The present invention may also be carried out as a processing method executed by the object information acquiring apparatus. The above mentioned processing and units may freely be combined as long as technical inconsistencies are not generated.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-171679, filed on Aug. 26, 2014, which is hereby incorporated by reference herein in its entirety.

REFERENCE SIGNS LIST

10: LIGHT IRRADIATION UNIT
20: ACOUSTIC WAVE DETECTION UNIT
30: SIGNAL PROCESSING UNIT

The invention claimed is:

1. An object information acquiring apparatus, comprising:
an irradiating unit configured to irradiate an object with pulsed light;
an acoustic wave detection unit configured to detect an acoustic wave generated from the object irradiated with the pulsed light and convert the acoustic wave into an electric signal;
a storage unit configured to store a normalized light fluence distribution, which is a light fluence distribution normalized for a region of a predetermined size; and
a processing unit configured to acquire characteristic information on the object using the stored normalized light fluence distribution and the electric signal,
wherein
the irradiating unit irradiates the object with the pulsed light at a plurality of irradiation positions, and
the processing unit uses same normalized light fluence distribution for the plurality of irradiation positions.

2. The object information acquiring apparatus according to claim 1, further comprising an irradiating light intensity acquiring unit configured to acquire the irradiating light intensity of the pulsed light emitted from the irradiating unit before irradiation of the object,
wherein
the storage unit stores a light fluence distribution, in which the irradiating light intensity of the pulsed light is normalized, as the normalized light fluence distribution, and
the processing unit acquires the characteristic information on the object using the stored normalized light fluence distribution, the irradiating light intensity acquired by the irradiating light intensity acquiring unit, and the electric signal.

3. The object information acquiring apparatus according to claim 2, wherein
the processing unit performs an operation to multiply the normalized light fluence distribution by the irradiating light intensity, and
acquires the characteristic information on the object, based on the electric signal and the normalized light fluence distribution after the operation.

4. The object information acquiring apparatus according to claim 2, wherein the processing unit acquires initial sound pressure distribution based on the electric signal, performs an operation to divide the initial sound pressure distribution by the irradiating light intensity, and acquires the characteristic information on the object, based on the normalized light fluence distribution and the initial sound pressure distribution after the operation.

5. The object information acquiring apparatus according to claim 2, wherein the processing unit performs an operation to divide the electric signal by the irradiating light intensity, and acquires the characteristic information on the object, based on the normalized light fluence distribution and the electric signal after the operation.

6. The object information acquiring apparatus according to claim 2, wherein
the irradiating light intensity acquiring unit detects a part of the pulsed light with which the object has been irradiated, and estimates the irradiating light intensity of the pulsed light with which the object has been irradiated, based on a result of the detection.

7. The object information acquiring apparatus according to claim 6, further comprising an optical element that branches a part of the pulsed light that the irradiating unit radiates, and guides the branched light to the irradiating light intensity acquiring unit.

8. The object information acquiring apparatus according to claim 1, wherein
the irradiating unit irradiates the object with the pulsed light for a plurality of times, and
the processing unit acquires the normalized light fluence distribution based on a specific pulsed light radiated at any timing.

9. The object information acquiring apparatus according to claim 8, wherein
the acoustic wave detection unit detects an acoustic wave generated by irradiation of pulsed light other than the specific pulsed light into the object, and converts the acoustic wave into an electric signal, and
the processing unit acquires the characteristic information on the object, based on the electric signal that originated from the pulsed light other than the specific pulsed light, and the normalized light fluence distribution.

10. The object information acquiring apparatus according to claim 1, further comprising a scanning mechanism that allows the irradiating unit to implement scanning, and the irradiating unit irradiates the object with pulsed light for a plurality of times while changing the irradiation position of the pulsed light.

11. The object information acquiring apparatus according to claim 1, further comprising a shape acquiring unit that acquires a shape of an irradiated surface irradiated with the pulsed light,
wherein the processing unit corrects the normalized light fluence distribution based on the shape of the irradiated surface, and acquires the characteristic information on the object, based on the corrected normalized light fluence distribution and the electric signal.

12. The object information acquiring apparatus according to claim 11, wherein the processing unit performs correction to match the shape of the normalized light fluence distribution with the shape of the irradiated surface.

13. A processing method to acquire characteristic information on an object irradiated with pulsed light based on an electric signal outputted by detecting an acoustic wave generated from the object, the method comprising:
a step of reading a normalized light fluence distribution, which is a light fluence distribution normalized for a region of a predetermined size, and is stored in a storage unit; and
a step of acquiring the characteristic information on the object using the normalized light fluence distribution and the electric signal,
wherein
the object is irradiated with the pulsed light at a plurality of irradiation positions; and the same normalized light fluence distribution is used for the plurality of irradiation positions.

14. The processing method according to claim 13, further comprising a step of acquiring irradiating light intensity of the pulsed light before irradiation of the object, wherein in the step of acquiring the characteristic information on the object, the characteristic information on the object is acquired using the normalized light fluence distribution, the irradiating light intensity and the electric signal.

15. A non-transitory computer readable storing medium recording a computer program for causing a computer to perform a processing method to acquire characteristic information on an object irradiated with pulsed light based on an electric signal outputted by detecting an acoustic wave generated from the object, the processing method comprising:
   a step of reading a normalized light fluence distribution, which is a light fluence distribution normalized for a region of a predetermined size, and is stored in a storage unit; and
   a step of acquiring the characteristic information on the object using the normalized light fluence distribution and the electric signal,
   wherein
      the object is irradiated with the pulsed light at a plurality of irradiation positions; and
      same normalized light fluence distribution is used for the plurality of irradiation positions.

16. An apparatus for acquiring characteristic information on an object based on an electric signal outputted by detecting an acoustic wave generated by irradiating the object with a pulsed light multiple times, the apparatus comprising:
   a processing unit configured to:
      acquire information on a normalized light fluence distribution, the normalized light fluence distribution being a light fluence distribution normalized for a region of a predetermined size, and
      calculate the characteristic information on the object using the information on the normalized light fluence distribution and the electric signal,
   wherein the processing unit is configured to iteratively use the normalized light fluence distribution for the pulsed light with which the object is irradiated multiple times.

17. The apparatus according to claim 16, wherein the processing unit is further configured to:
   acquire information on an intensity of the pulsed light emitted from an irradiating unit, and
   calculate the normalized light fluence distribution in which the intensity of the pulsed light is normalized on the basis of the information on the intensity of the pulsed light emitted from the irradiating unit.

18. The apparatus according to claim 16, wherein the processing unit is further configured to:
   acquire information on an intensity of the pulsed light when the object is irradiated with the pulsed light, and
   calculate the characteristic information on the object using the normalized light fluence distribution, the information on the intensity of the pulsed light when the object is irradiated with the pulsed light, and the electric signal.

19. The apparatus according to claim 16, wherein the processing unit is further configured to:
   calculate a normalized irradiating light fluence distribution by normalizing irradiating light fluence distribution of the pulsed light on the surface of the object irradiated with the pulsed light at a first timing on the basis of total light intensity of the pulsed light with which the object is irradiated at the first timing as a unit light intensity,
   calculate the normalized light fluence distribution of the pulse light with which the object is irradiated at the first timing by using the normalized irradiating light fluence distribution,
   calculate a light fluence distribution in the object of the pulse light with which the object is irradiated at a second timing by multiplying the normalized light fluence distribution by total light intensity of the pulsed light with which the object is irradiated at the second timing which is different from the first timing, and
   calculate the characteristic information on the object by using the light fluence distribution and a detected electric signal of the acoustic wave generated from the object by irradiating the object with the pulsed light at the second timing.

20. The apparatus according to claim 16, wherein the processing unit is further configured to:
   acquire information on a shape of an irradiated surface irradiated with the pulsed light,
   correct the normalized light fluence distribution based on the information on the shape of the irradiated surface, and
   calculate the characteristic information on the object, based on the normalized light fluence distribution which is corrected and the electric signal.

21. The apparatus according to claim 20, wherein the processing unit is further configured to correct the normalized light fluence distribution so that the shape of the normalized light fluence distribution corresponds to the shape of the irradiated surface.

* * * * *